United States Patent
Sugiyama et al.

(10) Patent No.: US 7,745,473 B2
(45) Date of Patent: Jun. 29, 2010

(54) INDOLE DERIVATIVE FOR ALKYLATING SPECIFIC BASE SEQUENCE OF DNA AND ALKYLATING AGENT AND DRUG CONTAINING THE DERIVATIVE

(75) Inventors: Hiroshi Sugiyama, Kyoto (JP); Toshikazu Bando, Kyoto (JP)

(73) Assignee: Kyoto University, Kyoto (JP)

( * ) Notice: Subject to any disclaimer, the term of this patent is extended or adjusted under 35 U.S.C. 154(b) by 13 days.

(21) Appl. No.: 10/598,789

(22) PCT Filed: Mar. 10, 2005

(86) PCT No.: PCT/JP2005/004250

§ 371 (c)(1), (2), (4) Date: Sep. 12, 2006

(87) PCT Pub. No.: WO2005/087762

PCT Pub. Date: Sep. 22, 2005

(65) Prior Publication Data

US 2007/0191260 A1     Aug. 16, 2007

(30) Foreign Application Priority Data

Mar. 13, 2004 (JP) .............................. 2004-114793

(51) Int. Cl.
| | |
|---|---|
| A61K 31/7052 | (2006.01) |
| A61K 31/407 | (2006.01) |
| A61K 31/4178 | (2006.01) |
| A61K 31/405 | (2006.01) |
| C07D 403/14 | (2006.01) |
| C07D 233/54 | (2006.01) |
| C07D 233/06 | (2006.01) |

(52) U.S. Cl. ........................ 514/397; 514/410; 514/411; 548/311.1; 548/420; 548/431; 548/465

(58) Field of Classification Search ................ 514/419, 514/422, 397, 414, 410, 411; 548/427, 420, 548/492, 518
See application file for complete search history.

(56) References Cited

U.S. PATENT DOCUMENTS 5,843,937 A * 12/1998 Wang et al. ................. 514/202

(Continued)

FOREIGN PATENT DOCUMENTS

JP       11-500427 A       1/1999

(Continued)

OTHER PUBLICATIONS

Boger et al, J. Org. Chem., 2001, 66, p. 6654-6661.*
Wikipedia, Gene.*

(Continued)

Primary Examiner—Yong Chu
(74) Attorney, Agent, or Firm—Sughrue Mion, PLLC

(57) ABSTRACT

There is provided a novel pyrrole-imidazole polyamide compound for alkylating the specific base sequence of DNA, the polyamide compound being capable of being synthesized through fewer reaction steps than known hybrid molecules and having a combination of a high reactivity in DNA alkylation and the ability to recognize a sequence. Furthermore, there is provided an alkylating agent and a molecule serving as a drug, the alkylating agent and the molecule containing the polyamide compound.

An indole derivative is represented by general formula (1):

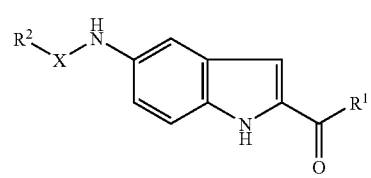

(1)

wherein $R^1$ represents a functional group for alkylating DNA; $R^2$ represents a hydrogen atom, an alkyl group, or an acyl group; and X represents a divalent group having one constitutional unit or having two or more constitutional units which may be the same or different, the constitutional unit being represented by the following formula:

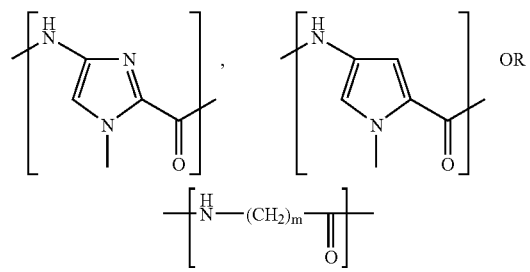

(wherein m is an integer of 0 to 10), wherein among the constitutional units, a terminal constitutional unit adjacent to $R^2$ may be a constitutional unit represented by the following formula:

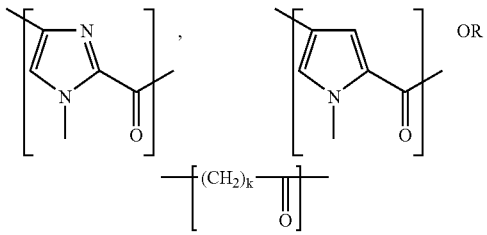

(wherein k is an integer of 0 to 10).

20 Claims, 6 Drawing Sheets

U.S. PATENT DOCUMENTS 6,281,354 B1 * 8/2001 Boger .................. 540/576

FOREIGN PATENT DOCUMENTS

| JP | 2000-506168 A | 5/2000 | | |
|---|---|---|---|---|
| JP | 2000-511893 A | 9/2000 | | |
| JP | 2001-519412 A | 10/2001 | | |
| WO | 00/15641 A | 3/2000 | | |
| WO | 03/000683 A1 | 1/2003 | | |
| WO | 03/022806 A2 | 3/2003 | | |
| WO | WO 03/022806 A2 | 3/2003 | | |
| WO | WO03022806 | * | 3/2003 | .............. 514/419 |
| WO | WO 03022806 A2 * | 3/2003 | | |
| WO | 03/072058 A2 | 9/2003 | | |
| WO | WO 03072058 A2 * | 9/2003 | | |

OTHER PUBLICATIONS

Sasaki et al. Nucleic Acids Symposium Series, No. 48, pp. 205-206, 2004.*

Boger et al., J org. Chem., 2001, vol. 66, p. 6654-6661.*

Gene, Wikipedia Encyclopedia, 2008.*

J.M. Turner, et al. "Recognition of Seven Base Pair Sequences in the Minor Groove of DNA by Ten-Ring Pyrrole-Imidazole Polyamide Hairpins", J. Am. Chem. Soc., (1997), 119, pp. 7636-7644 with Abstract.

R. Clairac, et al. "NMR Characterization of Hairpin Polyamide Complexes with the Minor Groove of DNA", Journal of the American Chemical Society, vol. 119, No. 34, Aug. 27, 1997 with Abstract.

A. Chang, et al. "Strand Selective Cleavage of DNA by Diastereomjers of Hairpin Polyamide-*seco*-CBI Conjugates", J. Am. Chem. Soc., (2000), 122, pp. 4856-4864 with Abstract.

Z. Tao, et al. "Rational Design of Sequences-Specific DNA Alkylating Agents Based on Duocarmycin A and Pyrrole-Imidazole Hairpin Polyamides", J. Am. Chem. Soc., (1999), 121, pp. 4961-4967 with Abstract.

Z. Tao, et al. "Highly Cooperative DNA Dialkylation by the Homodimer of Imidazole-Pyrrole Diamide-CPI Conjugate with Vinyl Linker", J. Am. Chem. Soc., (2000), 122, pp. 1602-1608 with Abstract.

T. Bando, et al. "Molecular Design of a Pyrrole-Imidazole Hairpin Polyamides for Effective DNA Alkylation", Chem.Eur. J., (2002), 8, No. 20, pp. 4781-4790 with Abstract.

D. Boger, et al. "An Improved Synthesis of 1,2,9,9a-Tetrahydrocyclopropa[c]benz[e]indol-4-one (CBI): A Simplified Analogue of the CC-1065 Alkylation Subunit", J. Org. Chem., (1992), 57, pp. 2873-2876.

D. Boger, et al. "An Efficient Synthesis of 1,2,9,9a-Tetrahydrocyclopropa[c]benz[e]indol-4-one (CBI): An Enhanced and Simplified Analog of the CC-1065 and Duocarmycin Alkylation Subunits", J. Org. Chem., (1995), 60, pp. 1271-1275.

D. Boger, et al. "Synthesis of *N*-(*tert*-Butyloxycarbonyl)-CBI, CBI, CBI-CDPI$_1$, and CBI-CDPI$_2$: Enhanced Functional Analogues of CC-1065 Incorporating the 1,2,9,9a-Tetrahydrocyclopropa[*c*]benz[*e*]indol-4-one (CBI) Left-Hand Subunit", J. Org. Chem., (1990), 55, pp. 5823-5832.

* cited by examiner

```
                        SEQUENCE LISTING

<160> NUMBER OF SEQ ID NOS: 19

<210> SEQ ID NO 1
<211> LENGTH: 450
<212> TYPE: DNA
<213> ORGANISM: Artificial Sequence
<220> FEATURE:
<223> OTHER INFORMATION: Synthetic construct

<400> SEQUENCE: 1
agaatcaggg gataacgcag gaaagaacat gtgagcaaaa ggccagcaaa aggccaggaa     60
ccgtaaaaag gccgcgttgc tggcgttttt ccataggctc cgcccccctg acgagcatca    120
caaaaatcga cgctcaagtc agaggtggcg aaacccgaca ggactataaa gataccaggc    180
gtttccccct ggaagctccc tcgtgcgctc tcctgttccg accctgccgc ttaccggata    240
cctgtccgcc tttctccctt cgggaagcgt ggcgctttct caatgctcac gctgtaggta    300
tctcagttcg gtgtaggtcg ttcgctccaa gctgggctgt gtgcacgaac cccccgttca    360
gcccgaccgc tgcgccttat ccggtaacta tcgtcttgag tccaacccgg taagacacga    420
cttatcgcca ctggcagcag ccactggtaa                                     450

<210> SEQ ID NO 2
<211> LENGTH: 20
<212> TYPE: DNA
<213> ORGANISM: Artificial Sequence
<220> FEATURE:
<223> OTHER INFORMATION: Synthetic construct

<400> SEQUENCE: 2
agaatcaggg gataacgcag                                                 20

<210> SEQ ID NO 3
<211> LENGTH: 20
<212> TYPE: DNA
<213> ORGANISM: Artificial Sequence
<220> FEATURE:
<223> OTHER INFORMATION: Synthetic construct

<400> SEQUENCE: 3
ttaccagtgg ctgctgccag                                                 20

<210> SEQ ID NO 4
<211> LENGTH: 450
```

```
<212> TYPE: DNA
<213> ORGANISM: Artificial Sequence
<220> FEATURE:
<223> OTHER INFORMATION: Synthetic construct

<400> SEQUENCE: 4
tgctggcctt ttgctcacat gttctttcct gcgttatccc ctgattctgt ggataaccgt    60
attaccgcct ttgagtgagc tgataccgct cgccgcagcc gaacgaccga gcgcagcgag   120
tcagtgagcg aggaagcgga agagcgccca atacgcaaac cgcctctccc cgcgcgttgg   180
ccgattcatt aatgcagctg gcacgacagg tttcccgact ggaaagcggg cagtgagcgc   240
aacgcaatta atgtgagtta gctcactcat taggcacccc aggctttaca ctttatgctt   300
ccggctcgta tgttgtgtgg aattgtgagc ggataacaat ttcacacagg aaacagctat   360
gaccatgatt acgaattcga gctcggtacc cggggatcct ctagagtcga cctgcaggca   420
tgcaagcttg cactggccg tcgttttaca                                     450

<210> SEQ ID NO 5
<211> LENGTH: 21
<212> TYPE: DNA
<213> ORGANISM: Artificial Sequence
<220> FEATURE:
<223> OTHER INFORMATION: Synthetic construct

<400> SEQUENCE: 5
tgctggcctt ttgctcacat g                                              21

<210> SEQ ID NO 6
<211> LENGTH: 19
<212> TYPE: DNA
<213> ORGANISM: Artificial Sequence
<220> FEATURE:
<223> OTHER INFORMATION: Synthetic construct

<400> SEQUENCE: 6
tgtaaaacga cggccagtg                                                 19

<210> SEQ ID NO 7
<211> LENGTH: 450
<212> TYPE: DNA
<213> ORGANISM: Artificial Sequence
<220> FEATURE:
<223> OTHER INFORMATION: Synthetic construct

<400> SEQUENCE: 7
tgtaaaacga cggccagtgc caagcttgca tgcctgcagg tcgactctag aggatccccg    60
ggtaccgagc tcgaattcgt aatcatggtc atagctgttt cctgtgtgaa attgttatcc   120
gctcacaatt ccacacaaca tacgagccgg aagcataaag tgtaaagcct ggggtgccta   180
atgagtgagc taactcacat taattgcgtt gcgctcactg cccgctttcc agtcgggaaa   240
cctgtcgtgc cagctgcatt aatgaatcgg ccaacgcgcg gggagaggcg gtttgcgtat   300
tgggcgctct tccgcttcct cgctcactga ctcgctgcgc tcggtcgttc ggctgcggcg   360
agcggtatca gctcactcaa aggcggtaat acggttatcc acagaatcag gggataacgc   420
aggaaagaac atgtgagcaa aaggccagca                                    450

<210> SEQ ID NO 8
<211> LENGTH: 537
<212> TYPE: DNA
<213> ORGANISM: Artificial Sequence
<220> FEATURE:
```

-continued

<223> OTHER INFORMATION: Synthetic construct

<400> SEQUENCE: 8

```
atcagggcaa ctcaaccctg tccgatttca acaaaacgct ggtcctttcc ggcaatcagg      60
cgggactgac ggcagatcgt atgctggtcc tgtccagagc cgggcaggcg gcagggctga     120
cgtttaacca gaccagcgag tcactcagcg cactggttaa ggcggggta agcggtgagg      180
ctcagattgc gtccatcagc cagagtgtgg cgcgtttctc ctctgcatcc ggcgtggagg     240
tggacaaggt cgctgaagcc ttcgggaagc tgaccacaga cccgacgtcg gggctgacgg     300
cgatggctcg ccagttccat aacgtgtcgg cggagcagat tgcgtatgtt gctcagttgc     360
agcgttccgg cgatgaagcc ggggcattgc aggcggcgaa cgaggccgca acgaaagggt     420
ttgatgacca gacccgccgc tgaaagagaa acatgggcac gctggagacc tgggcagaca    480
ggactgcgcg gcattcaaa tccatgtggg atgcggtgct ggatattggt cgtcctg        537
```

<210> SEQ ID NO 9
<211> LENGTH: 23
<212> TYPE: DNA
<213> ORGANISM: Artificial Sequence
<220> FEATURE:
<223> OTHER INFORMATION: Synthetic construct

<400> SEQUENCE: 9

```
atcagggcaa ctcaaccctg tcc                                              23
```

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10

```
caggacgacc aatatccagc                                                  20
```

<210> SEQ ID NO 11
<211> LENGTH: 994
<212> TYPE: DNA
<213> ORGANISM: Artificial Sequence
<220> FEATURE:
<223> OTHER INFORMATION: Synthetic construct

<400> SEQUENCE: 11

```
ccccaagggg ttatgctagt tattgctcag cggtggcagc agccaactca gcttcctttc      60
gggctttgtt agcagccgga tcctcagttg tacagttcat ccatgccatg tgtaatccca     120
gcagctgtta caaactcaag aaggaccatg tggtctctct tttcgttggg atctttcgaa     180
agggcagatt gtgtggacag gtaatggttg tctggtaaaa ggacagggcc atcgccaatt    240
ggagtatttt gttgataatg gtctgctagt tgaacgcttc catcttcaat gttgtggcgg     300
gtcttgaagt tcactttgat tccattcttt tgtttgtctg ccatgatgta tacattgtgt     360
gagttatagt tgtattccaa tttgtgtccc agaatgttgc catcttcctt gaagtcaata    420
cctttaact cgattctatt aacaagggta tcaccttcaa acttgacttc agcacgtgtc     480
ttgtagttgc cgtcatcttt gaagaagatg gtccttcct gtacataacc ttcgggcatg     540
gcactcttga aaagtcatg ccgtttcata tgatccgggt atcttgaaaa gcattgaaca     600
ccatagcaca gagtagtgac tagtgttggc catggaacag gcagtttgcc agtagtgcag     660
atgaacttca gggtaagttt tccgtatgtt gcatcacctt caccctctcc actgacagag    720
```

```
aacttgtggc cgttaacatc accatctaat tcaacaagaa ttgggacaac tccagtgaag    780
agttcttctc ctttgctagc catatgtata tctccttctt aaagttaaac aaaattattt    840
ctagagggga attgttatcc gctcacaatt cccctatagt gagtcgtatt aatttcgcgg    900
gatcgagatc tcgatcctct acgccgacg catcgtggcc ggcatcaccg cgccacagg     960 tgcggttgct ggcgcctata tcgccgacat cacc                                994
```

```
<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
ggtgatgtcg gcgatatagg                                                 20

<210> SEQ ID NO 13
<211> LENGTH: 20
<212> TYPE: DNA
<213> ORGANISM: Artificial Sequence
<220> FEATURE:
<223> OTHER INFORMATION: Synthetic construct

<400> SEQUENCE: 13
ccccaagggg ttatgctagt                                                 20

<210> SEQ ID NO 14
<211> LENGTH: 727
<212> TYPE: DNA
<213> ORGANISM: Artificial Sequence
<220> FEATURE:
<223> OTHER INFORMATION: Synthetic construct

<400> SEQUENCE: 14
cccattctaa actgtaccct gttacttatc cccttcctat gacatgaact taatcataga    60
aaagaagggg aaagaaaaca tcaagcgtcc catagactca ccctgaagtt ctcaggatcc    120
acgtgcagct tgtcacagtg cagctcactc agtgtggcaa aggtgccctt gaggttgtcc    180
aggtgagtta ggccatcact aaaggcaccg agcactttct tgccatgagc cttcacctta    240
gggttgccca taacagcatc aggagtggac agatccccaa aggactcaaa gaacctctgg    300
gtccaagggt agaccaccag cagcctaagg gtgggaaaat agaccaatag cagagagag     360 tcagtgccta tcagaaaccc aagagtcttc tctgtctcca catgcccagt ttctattggt    420
ctccttaaac ctgtcttgta accttgatac caacctgccc agggcctcac caccaacttc    480
atccacgttc accttgcccc acagggcagt aacggcagac ttctcctcag gagtcagatg    540
caccatggtg tctgtttgag gttgctagtg aacacagttg tgtcagaagc aaatgtaagc    600
aagcttcgca gacagcgatg cggaagagag tgaggacgaa cgcgccccca ccccttttta    660
tagcccccct tcaccaacac ccggtcacgt ggcctacacc tataaaccaa tcaccttcct    720
tgatgcc                                                               727

<210> SEQ ID NO 15
<211> LENGTH: 20
<212> TYPE: DNA
<213> ORGANISM: Artificial Sequence
<220> FEATURE:
<223> OTHER INFORMATION: Synthetic construct
```

```
<400> SEQUENCE: 15
cccattctaa actgtaccct                                                    20

<210> SEQ ID NO 16
<211> LENGTH: 21
<212> TYPE: DNA
<213> ORGANISM: Artificial Sequence
<220> FEATURE:
<223> OTHER INFORMATION: Synthetic construct

<400> SEQUENCE: 16
ggcatcaagg aaggtgattg g                                                  21

<210> SEQ ID NO 17
<211> LENGTH: 446
<212> TYPE: DNA
<213> ORGANISM: Artificial Sequence
<220> FEATURE:
<223> OTHER INFORMATION: Synthetic construct

<400> SEQUENCE: 17
ggccagtgaa ttgtaatacg actcactata gggcgaattg ggccctctag atgcatgctc         60
gagcggccgc cagtgtgatg gatatctgca gaattcggct tagtcacgac gttgtaggcc        120
taaccctaac cctaacccta accctaaccc taaccctaac cctaacccta accctaaccc        180
taaccctaac cctaacccta accctaaccc taaccctaac cctaacccta accctaaccc        240
taaccctaac cctaacccta accctaaccc gggtcatagc tgtttcctga agccgaattc        300
cagcacactg gcggccgtta ctagtggatc cgagctcggt accaagcttg gcgtaatcat        360
ggtcatagct gtttcctgtg tgaaattgtt atccgctcag aattccacac aacatacgag        420
ccggaagcat aaagtgtaaa gcctgg                                             446

<210> SEQ ID NO 18
<211> LENGTH: 20
<212> TYPE: DNA
<213> ORGANISM: Artificial Sequence
<220> FEATURE:
<223> OTHER INFORMATION: Synthetic construct

<400> SEQUENCE: 18
ggccagtgaa ttgtaatacg                                                    20

<210> SEQ ID NO 19
<211> LENGTH: 20
<212> TYPE: DNA
<213> ORGANISM: Artificial Sequence
<220> FEATURE:
<223> OTHER INFORMATION: Synthetic construct

<400> SEQUENCE: 19
ccaggcttta cactttatgc                                                    20
```

INDOLE DERIVATIVE FOR ALKYLATING SPECIFIC BASE SEQUENCE OF DNA AND ALKYLATING AGENT AND DRUG CONTAINING THE DERIVATIVE

This is a national stage application under 35 U.S.C. §371 of PCT/JP2005/004250 filed on Mar. 10, 2005, which claims priority from Japanese patent application 2004-114793 filed on Mar. 13, 2004, all of which are incorporated herein by reference.

TECHNICAL FIELD

The present invention relates to a novel indole derivative for alkylating a specific base sequence of deoxyribonucleic acid (DNA). The present invention also relates to an alkylating agent and a drug that contain the indole derivative. Specifically, the present invention relates to a novel indole derivative that particularly suppresses the occurrence of genetic abnormalities and has high anticancer activity and significantly high reactivity. The present invention also relates to an alkylating agent and a drug that contain the indole derivative.

BACKGROUND ART

Now that the elucidation of the gene arrangement of humans has been substantially completed, many researchers have focused on a molecule having the ability to specifically bind to a particular base sequence. Non-Patent Document 1 and the like show that Dervan et al. found that an antiparallel oriented "N-methylpyrrole"-"N-methylimidazole" polyamide (hereinafter, N-methylpyrrole being simply referred to as "pyrrole" or "Py"; and N-methylimidazole being simply referred to as "imidazole" or "Im") base-sequence-specifically binds to the minor groove of DNA. Furthermore, general rules that Py-Im recognizes a C-G base pair, Im-Py recognizes a G-C base pair, and Py-Py recognizes an A-T base pair or a T-A base pair have been derived.

Various hairpin polyamides and cyclic polyamides have been synthesized by introducing a covalent bond into Py-Im in order to prevent the loss of entropy due to binding and to achieve stronger binding and the ability to recognize a sequence. A β-linker (—NHCH$_2$CH$_2$CO—) and a γ-linker (—NHCH$_2$CH$_2$CH$_2$CO—) are typically known. It has been described that a hairpin polyamide containing the γ-linker (—NHCH$_2$CH$_2$CH$_2$CO—) particularly has excellent binding ability and recognition ability. In addition, the structure of a complex between the hairpin polyamide containing the γ-linker and DNA has been determined (see Non-Patent Document 2). β-β recognizes an A-T base pair or a T-A base pair. Similarly, the γ-linker recognizes an A-T base pair or a T-A base pair. The γ-linker has a γ-turn structure represented by the trifurcate portion of a bent hairpin model.

These molecules each have an association constant and specificity comparable to a transcription factor and the like. However, the regulation of gene expression is performed by inhibiting binding of the transcription factor. Thus, base sequences that can be targeted is significantly limited (for example, see Non-Patent Document 3).

The inventors have developed a hybrid molecule of a Py-Im polyamide bound to a segment A (Du) serving as an alkylating moiety of duocarmycin A, which is an antibiotic, and filed an application (for example, Patent Document 1). The hybrid molecule selectively alkylated one site of a DNA fragment of 450 base pairs on the basis of the sequence recognition ability of the Py-Im polyamide (for example, see Non-Patent Document 4). However, completion of the reaction requires several days. Furthermore, the reaction efficiency was as low as several percent.

In contrast, the inventors found that ImPyLDu86 containing a vinyl linker (L) disposed between a functional group (hereinafter, referred to as an "alkylating moiety") for alkylating DNA and the Py-Im polyamide dimerizes and selectively reacts with both chains at sites thereof located 5 base pairs apart in a 5'-YG(A/T)CR-3' sequence (wherein Y represents a pyrimidine base; and R represents a purine base) at a low concentration to cause alkylation with an efficiency as high as 70%. That is, the inventors found considerable improvement in reactivity and efficiency by introducing the linker moiety (for example, see Non-Patent Document 5).

Patent Document 1: International Publication No. WO00/15641

Non-Patent Document 1: J. Am. Chem. Soc. 1997, 119, 7636

Non-Patent Document 2: J. Am. Chem. Soc. 1997, 119, 7909

Non-Patent Document 3: J. Am. Chem. Soc. 2000, 122, 4856

Non-Patent Document 4: J. Am. Chem. Soc. 1999, 121, 4961

Non-Patent Document 5: J. Am. Chem. Soc. 2000, 122, 1602

DISCLOSURE OF INVENTION

Problems to be Solved by the Invention

However, the hybrid molecule described in Non-Patent Document 5 has problems related to difficulty of synthesis, the lability of the linker moiety, the reactivity of the alkylating moiety, and the like.

Accordingly, it is an object of the present invention to provide a novel pyrrole-imidazole polyamide compound for alkylating the specific base sequence of DNA, the polyamide compound being capable of being synthesized through fewer reaction steps than known hybrid molecules and having a combination of a high reactivity in DNA alkylation and the ability to recognize a sequence. Furthermore, it is an object of the present invention to provide an alkylating agent and a molecule serving as a drug, the alkylating agent and the molecule containing the polyamide compound.

Means for Solving the Problems

The inventors have conducted intensive studies and found that the use of a pyrrole-imidazole polyamide compound having an alkylating moiety at a terminus thereof via an indole linker solved the problems described above. This finding resulted in completion of the present invention.

That is, an indole derivative of the present invention is represented by general formula (1):

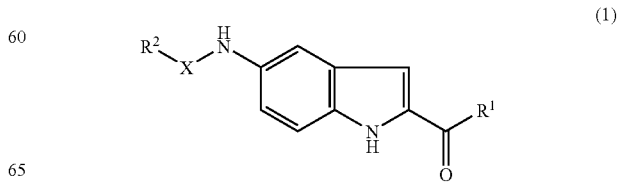

wherein R¹ represents a functional group for alkylating DNA; R² represents a hydrogen atom, an alkyl group, or an acyl group; and X represents a divalent group having one constitutional unit or having two or more constitutional units which may be the same or different, the constitutional unit being represented by the following formula:

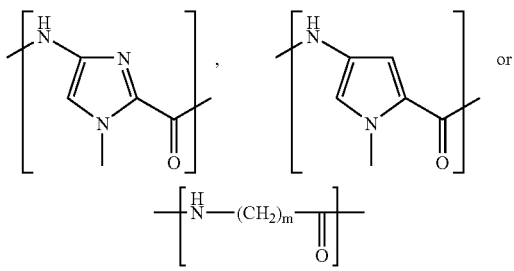

(wherein m is an integer of 0 to 10), wherein among the constitutional units, a terminal constitutional unit adjacent to R² may be a constitutional unit represented by the following formula:

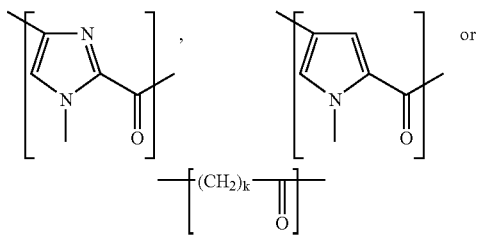

(wherein k is an integer of 0 to 10).

An alkylating agent of the present invention for alkylating DNA is composed of the indole derivative of the present invention described above.

An inventive drug contains the alkylating agent of the present invention and suppresses or activates the expression of a gene.

Advantages

An indole derivative of the present invention is a functional molecule selectively alkylating a specific base sequence present in a gene. The indole derivative can change a target base sequence by changing the configuration of imidazole, pyrrole, and the like in its molecule. Furthermore, a method for synthesizing the indole derivative is practical and highly applicable in view of the production of a wide variety of derivatives. Therefore, it is possible to logically design a drug on a genetic level, the drug being applicable to an important gene arrangement or an abnormal gene derived from a disease, such as cancer, in the human genome.

BEST MODE FOR CARRYING OUT THE INVENTION

Figure 1:
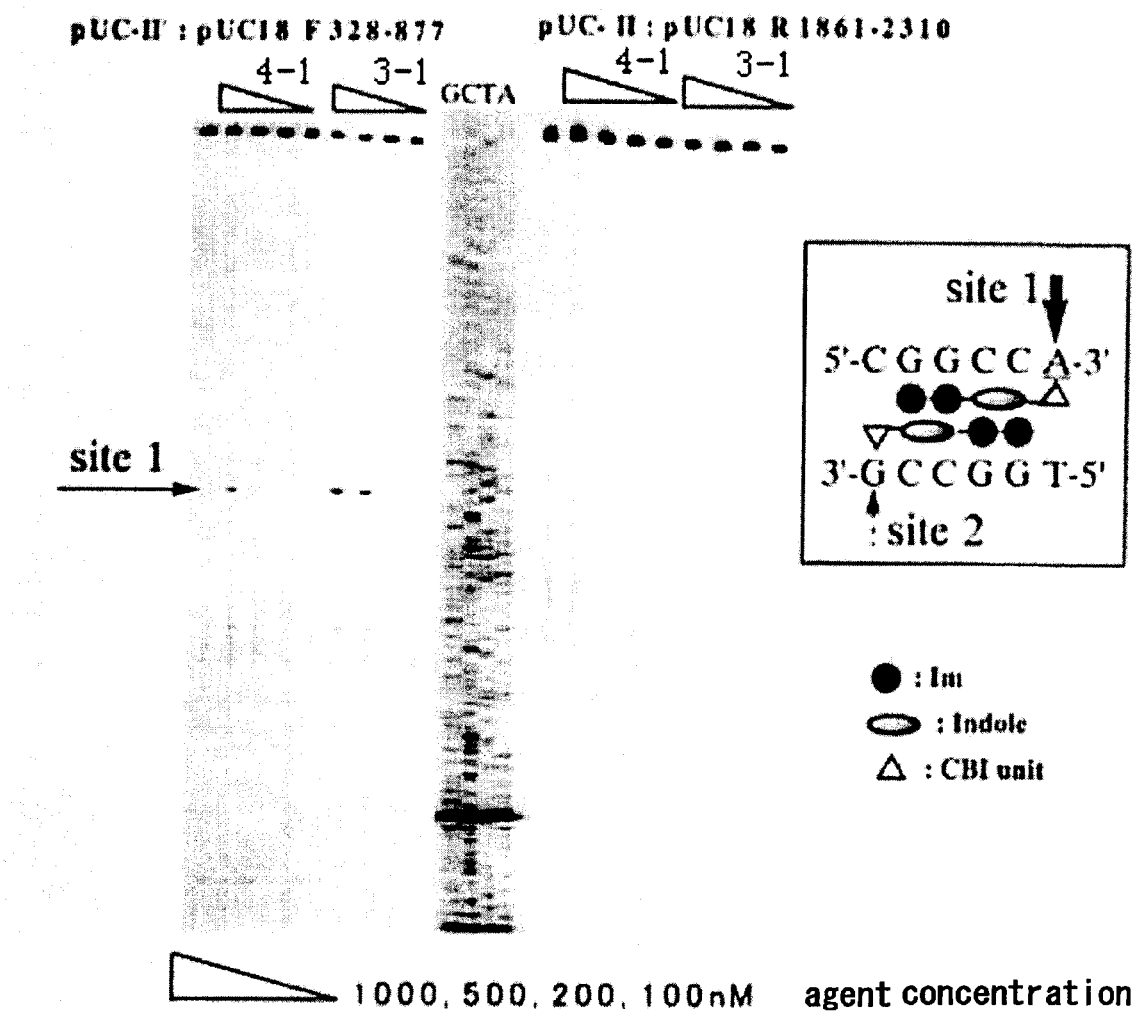
FIG. 1 shows abilities of compounds (4-1) and (3-1) of the present invention to DNA-sequence-specifically alkylate a long-chain DNA (pUC-II and pUC-II'); and a sequence recognition model thereof.

Preferred embodiments of the present invention will be described in detail below.

An indole derivative of the present invention is represented by general formula (1):

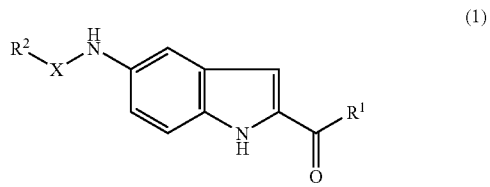

(1)

wherein X represents a divalent group having one constitutional unit or having two or more constitutional units which may be the same or different, the constitutional unit being represented by the following formula:

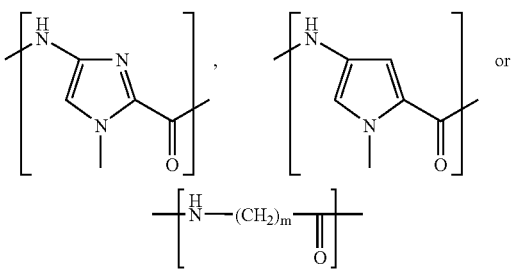

wherein among the constitutional units, a terminal constitutional unit adjacent to R² may be a constitutional unit represented by the following formula:

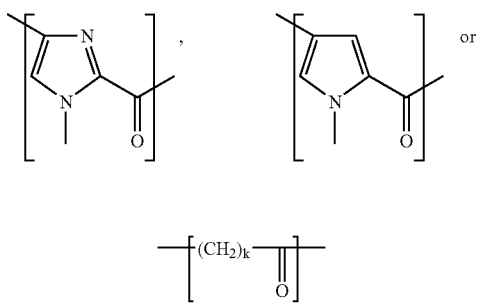

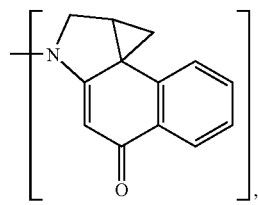

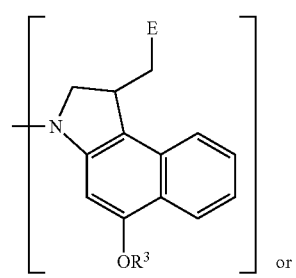

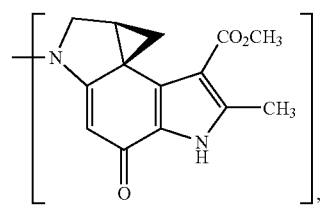

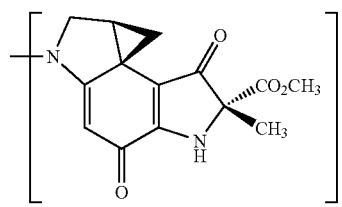

wherein m and k are each an integer of 0 to 10, preferably 1 to 6, and more preferably 2 to 3. Furthermore, the number of constitutional units is not particularly limited but appropriately selected depending on a DNA sequence targeted for alkylation. Usually, the number of constitutional units is preferably 1 to 20 and more preferably 2 to 7. The sequence of the constitutional units is not particularly limited but appropriately selected depending on a DNA sequence targeted for alkylation to design a polyamide.

A DNA sequence recognized by the indole derivative of the present invention complies with the known general rule in principle. That is, Py-Im recognizes a C-G base pair; Im-Py recognizes a G-C base pair; Py-Py recognizes an A-T base pair or a T-A base pair; and β-β, γ-γ, or the like recognizes an A-T base pair or a T-A base pair. Furthermore, β-β, γ-γ, or the like not only recognizes the base pair but also constitutes the trifurcate portion of a bent hairpin model. As has been generally known, in rare cases, a mismatch occurs depending on sequences around a target DNA sequence. For example, in an AT-rich sequence, Im-Py and the like adjacent to the γ-turn structure in a hairpin-shape molecule often misrecognize.

In an indole linker, which is the advantage of the compound of the present invention, two of Im, Py, and the like relative to one indole can form a pair. Two of Im, Py, and the like to form a pair are not necessarily needed. One of Im, Py, and the like may be used. Indole tends to recognize C or T similar to recognition by Py. Furthermore, the alkylating moiety of the indole derivative of the present invention alkylates the N-3 position of a purine base, in particular, the N-3 position of adenine.

The alkylating moiety represented by $R^1$ in the above-described formula (1) is not particularly limited. Any moiety having the abilities to recognize and alkylate a specific base sequence in DNA may be used. Preferred examples of the alkylating moiety, i.e., $R^1$, include moieties represented by the following formulae:

(2)

wherein in each of the moieties represented by formulae (2), (3), (4), and (5), a substituent may be introduced, and the structure of each moiety may be simplified within the range in which the alkylation reaction is not inhibited.

The moieties represented by formulae (2) and (5) described above are each CPI derived from duocarmycin A. Hereinafter, the moiety represented by formula (2) is referred to as "DU86". The moiety represented by formula (5) is referred to as "Du". Furthermore, 1,2,9,9a-tetrahydrocyclopropa[c]benzo[e]indol-4-one represented by formula (3) is referred to as "CBI". CBI represented by formula (3) includes optically isomeric moieties (3-S) and (3-R) represented by the following formulae:

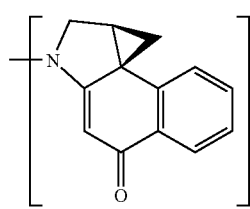

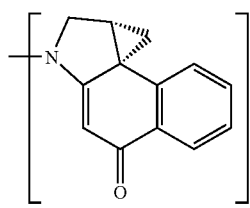

$R^3$ in formula (4) represents a hydrogen atom, a peptide chain, a carbohydrate chain, or a polyethylene glycol group.

Examples thereof include peptide chains, proteins, monosaccharides, disaccharides, polysaccharides, and polyethylene glycols. E represents an easily detachable substituent, such as a halogen atom, a mesyl group, or a tosyl group. Examples of halogen include bromine, fluorine, and iodine. Preferably, halogen is chlorine.

An example of the moiety represented by formula (4) is a moiety of 1-chloromethyl-5-hydroxy-1,2-dihydro-3H-benzo[e]indole (referred to as "seco-CBI") represented by formula (4-A):

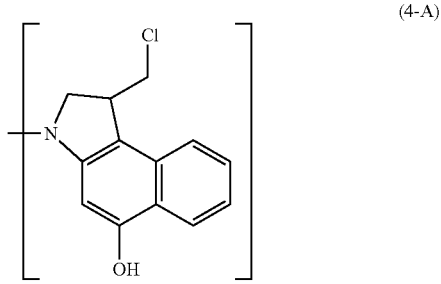

(4-A)

The moiety represented by formula (4-A) includes optically isomeric moieties represented by formulae (4-A-S) and (4-A-R):

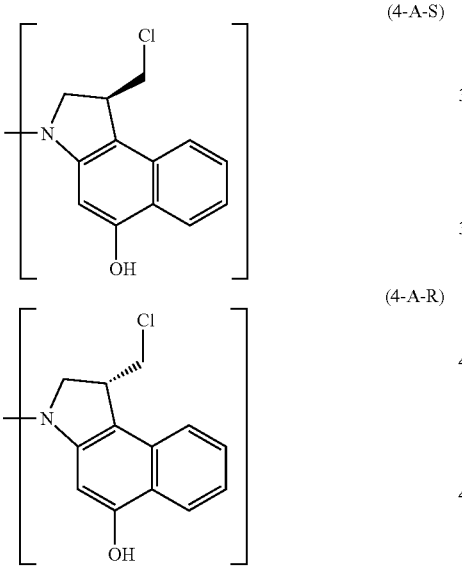

(4-A-S)

(4-A-R)

The moieties represented by formulae (3-S) and (3-R) can be prepared by treating the moieties represented by formulae (4-A-S) and (4-A-R) with a weak alkali as shown in the following reaction schemes:

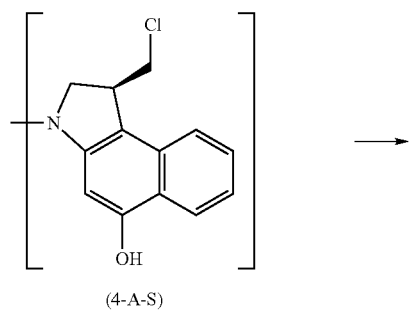

(4-A-S)

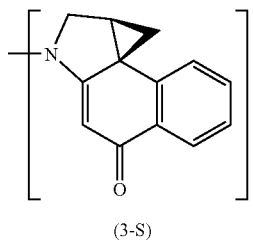

(3-S)

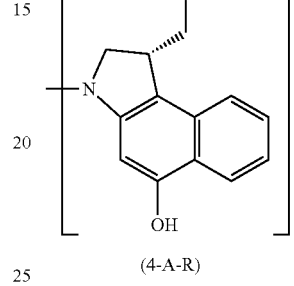

(4-A-R)

(3-R)

The moiety of S-CBI represented by formula (3-S) includes the three-membered ring having the same configuration as that of the naturally existing Du moiety represented by formula (5). The indole derivative represented by formula (1) in which $R^1$ is represented by formula (3-S) has alkylating activity. In contrast, the indole derivative represented by formula (1) in which $R^1$ is the moiety of R-CBI represented by formula (3-R) has significantly weak alkylating activity and is thus inactive.

$R^2$ in formula (1) represents a hydrogen atom, an alkyl group, or an acyl group. The alkyl group and the acyl group (portion excluding CO) usually has a carbon atom number of 1 to 20 and preferably 1 to 10. A linear or branched lower alkyl group having 1 to 6 carbon atoms is more preferred. Examples thereof include a methyl group, an ethyl group, a n-propyl group, an isopropyl group, a n-butyl group, an isobutyl group, a tert-butyl group, a pentyl group, and a hexyl group. The indole derivative represented by formula (1) in which $R^2$ is an acetyl group can be suitably used. Furthermore, each of an alkyl group and an acyl group may have a substituent.

Examples of the indole derivative represented by general formula (1) include compounds represented by the following formulae:

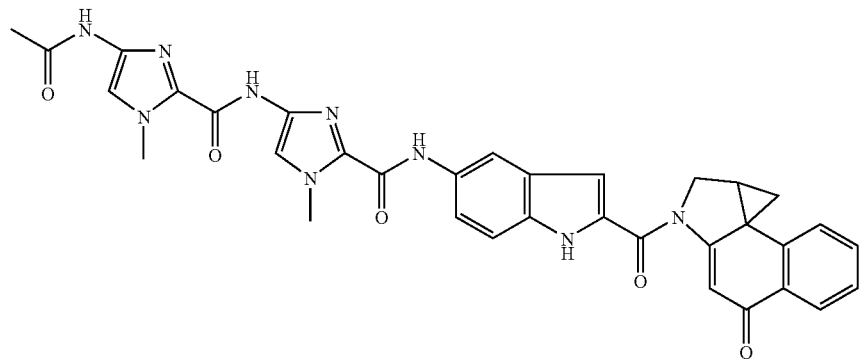
(3-1)
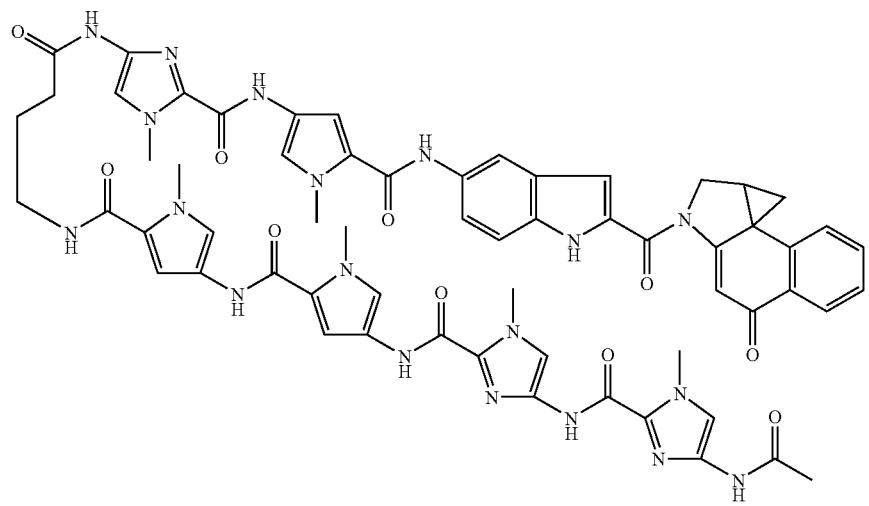
(3-2)
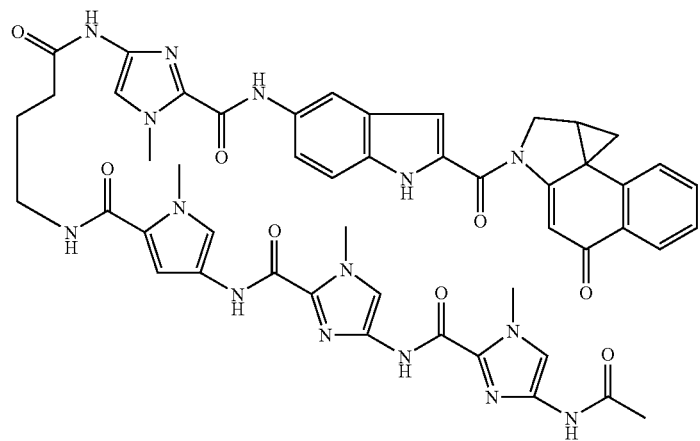
(3-3)

(3-4)
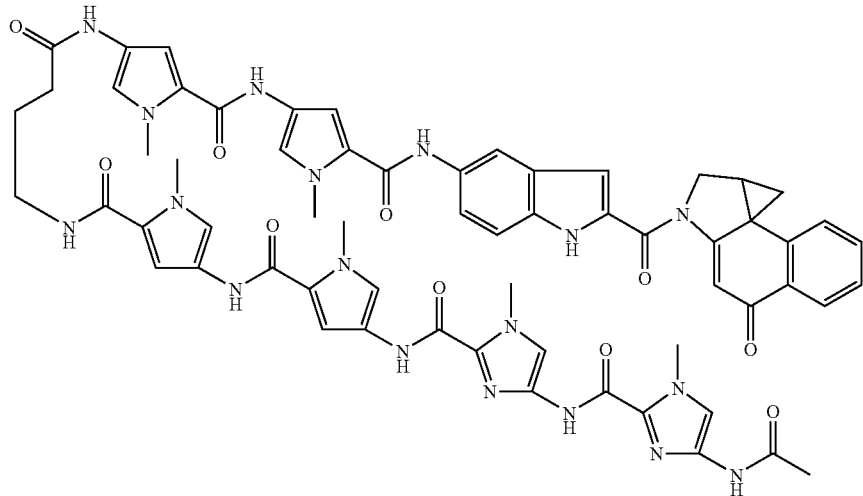
(3-5)
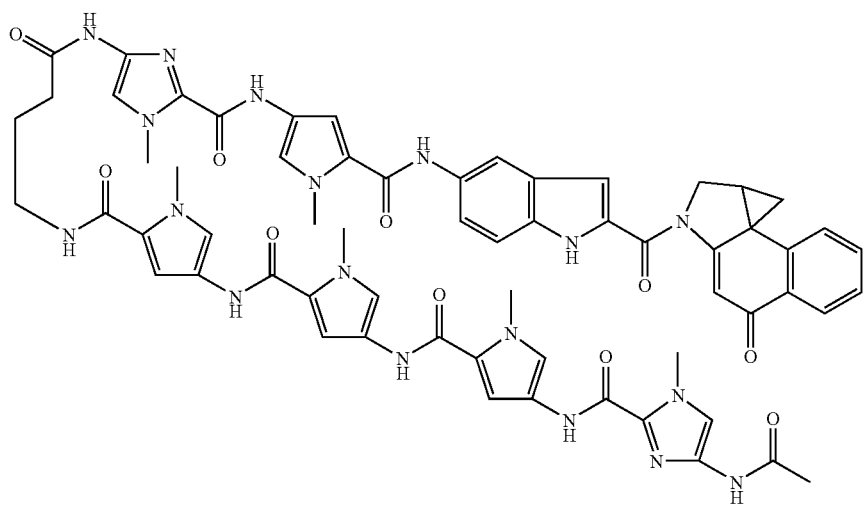
(3-6)
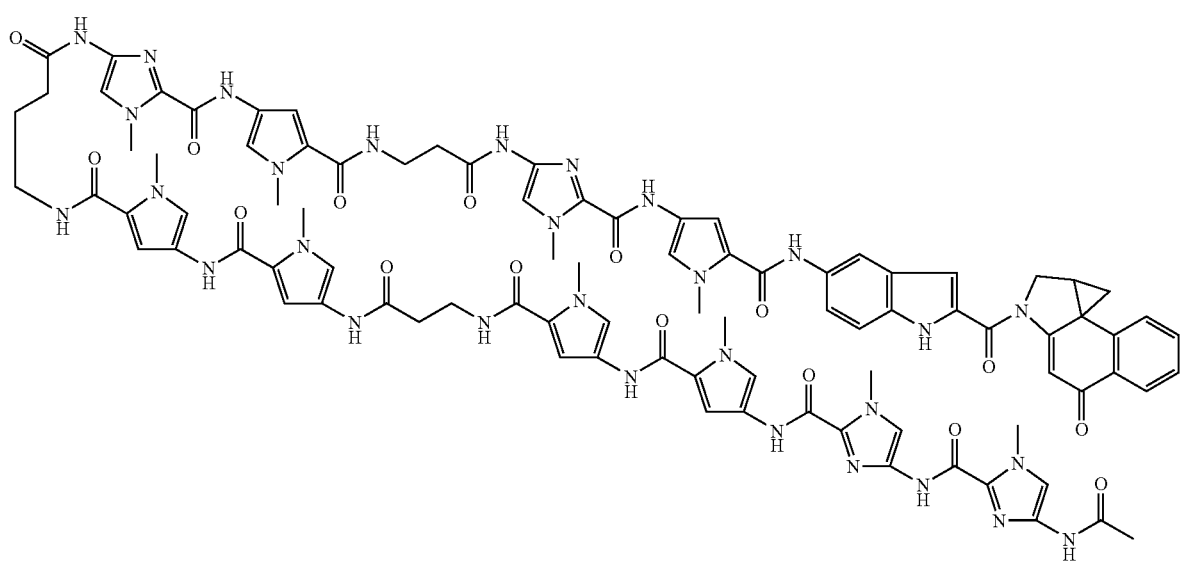

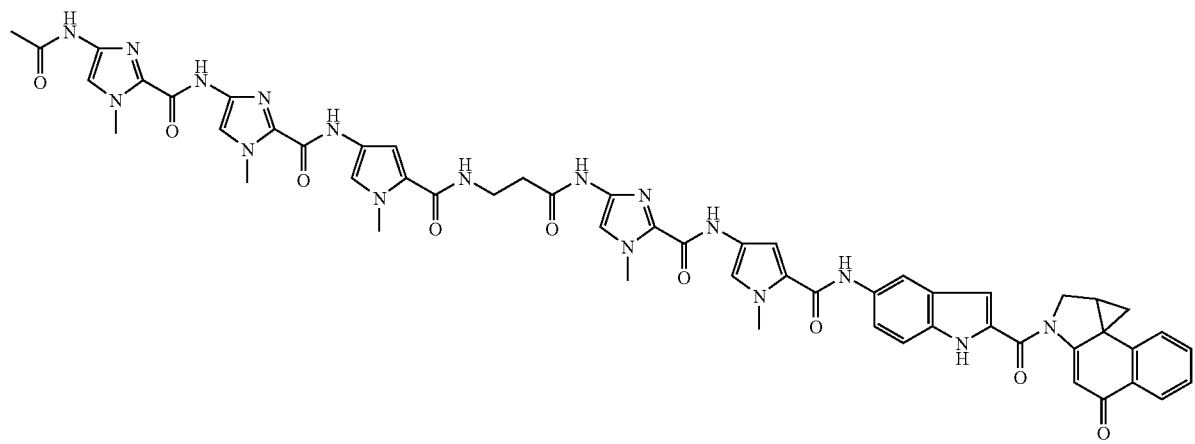
(3-7)
(wherein R¹ represents the moiety represented by formula (3); and R² represents an acyl group); and compounds represented by the following formulae:
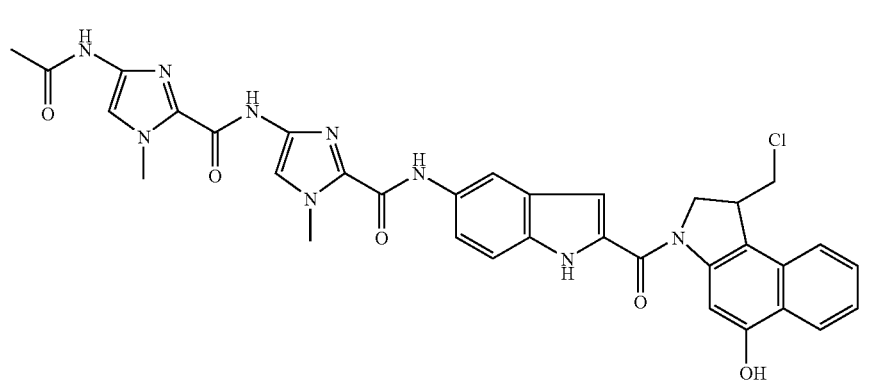
(4-1)
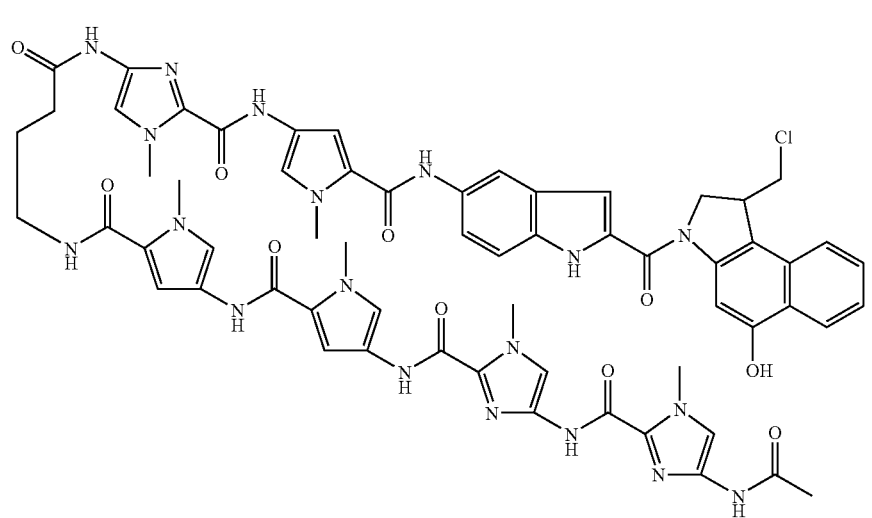
(4-2)

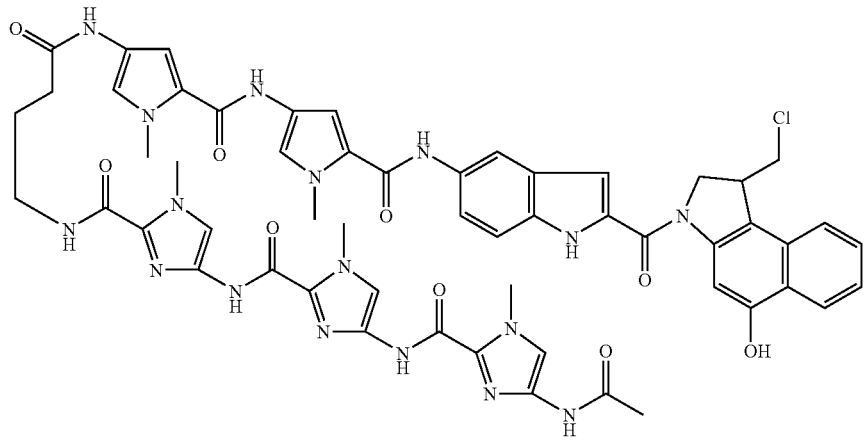

(wherein R¹ represents the moiety represented by formula (4-A); and R² represents an acyl group).

By taking compound (3-1) as an example, the outline of a method for synthesizing the indole derivative of the present invention will be described according to synthetic scheme 1. AcImImCO₂H (3-1-1) and amine compound (3-1-2) prepared from 5-nitroindole-2-carboxylic acid ethyl ester by catalytic reduction are dissolved in dimethylformamide (DMF). 0-(7-azabenzatriazol-1-yl)-1,1,3,3-tetramethyluronium hexafluorophosphate (HATU) functioning as a condensation agent and diisopropylethylamine (ⁱPr₂NEt) are added to the resulting solution to perform a condensation reaction into Py-Im indole ethyl ester (3-1-3). Compound (3-1-3) is subjected to alkaline hydrolysis to prepare carboxylic acid (3-1-4). Next, carboxylic acid (3-1-4) thus prepared is coupled to seco-CBI (3-1-5) that can be synthesized from commercially available 1,3-naphthalenediol, thereby preparing open-circular compound (4-1) as a compound of the present invention. Furthermore, open-circular compound (4-1) is treated with a weak alkali (NaHCO₃) in water to prepare circular compound (3-1) as a compound of the present invention.

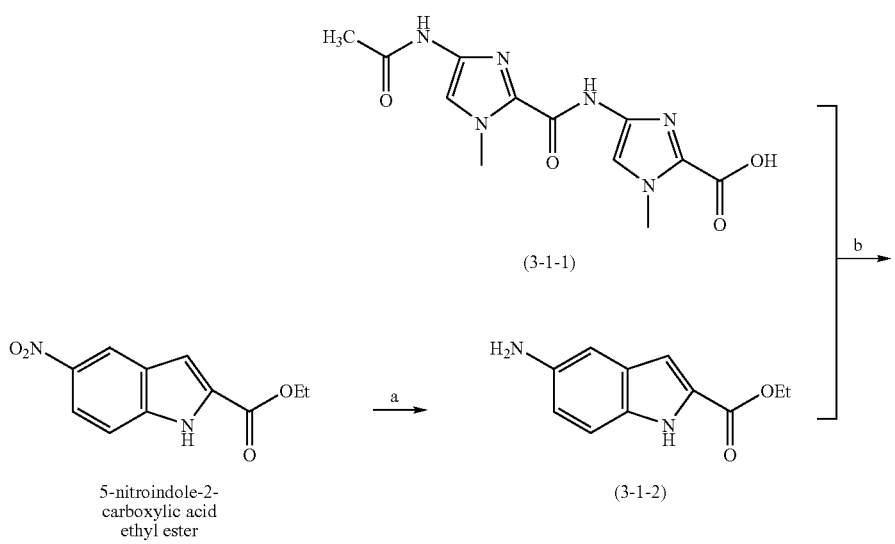

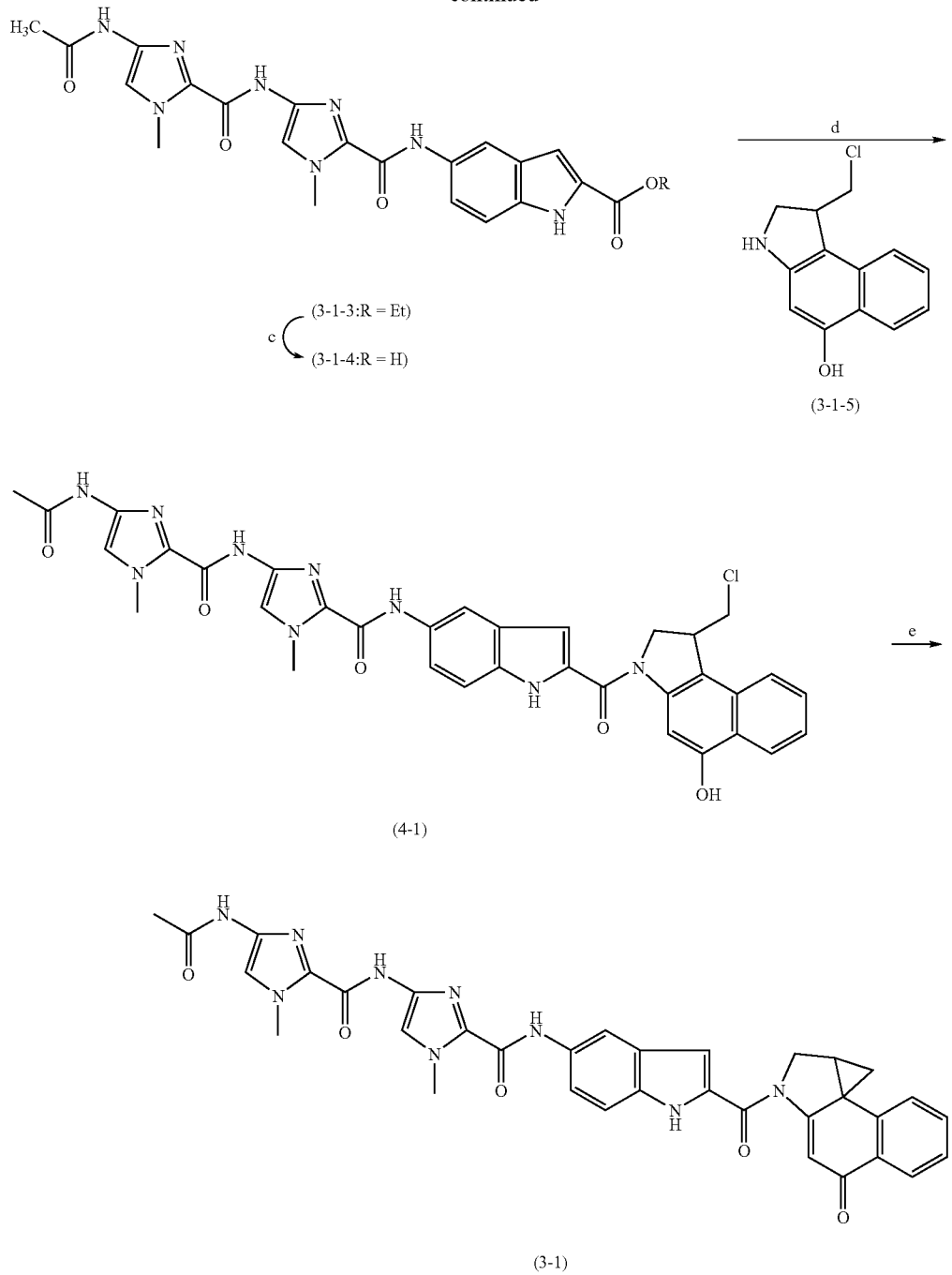

By taking compound (3-2) as an example, the outline of a method for synthesizing the indole derivative of the present invention will be described according to synthetic scheme 2. By applying Fmoc solid-phase synthesis to a Py-Im polyamide using an oxime resin, carboxylic acid (3-2-1) corresponding to the above-described hairpin Py-Im polyamide is prepared. After carboxylic acid (3-2-1) is converted into active At ester (3-2-2) using HATU in the reaction system, aminoindolecarboxylic acid (3-2-3) is added thereto to synthesize indolecarboxylic acid (3-2-4) at a time. Compound (3-2-4) is coupled to seco-CBI (3-1-5) that can be prepared from commercially available 1,3-naphthalenediol, thereby preparing open-circular compound (4-2) as the indole derivative of the present invention. Furthermore, open-circular compound (4-2) is treated with a weak alkali (NaHCO$_3$) in water to prepare circular compound (3-2) as the indole derivative of the present invention. Circular compounds (3-3), (3-4), (3-5), and the like as indole derivatives of the present invention can be prepared in the same way.

(Reaction Scheme 2)
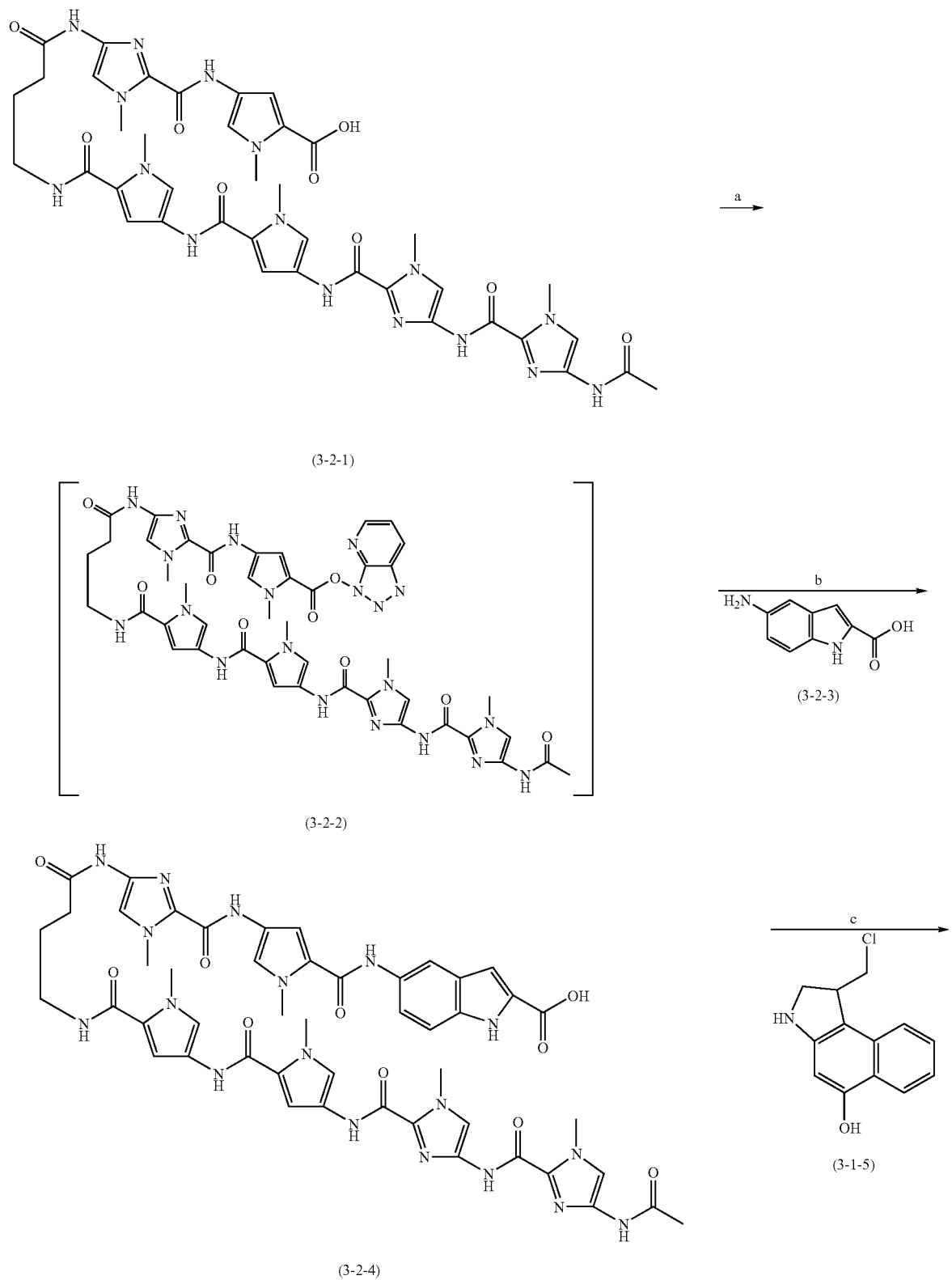

-continued

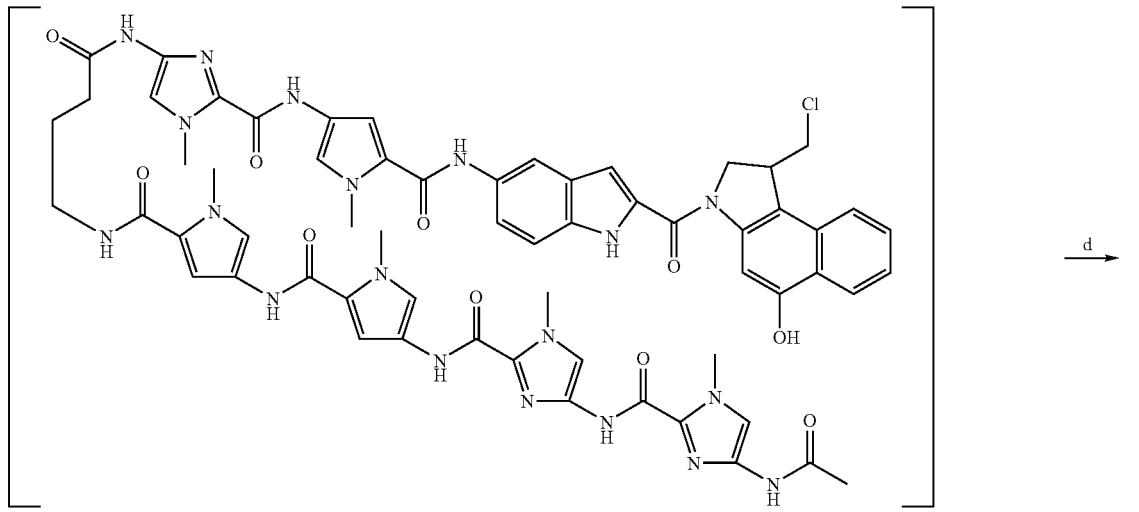

(4-2)

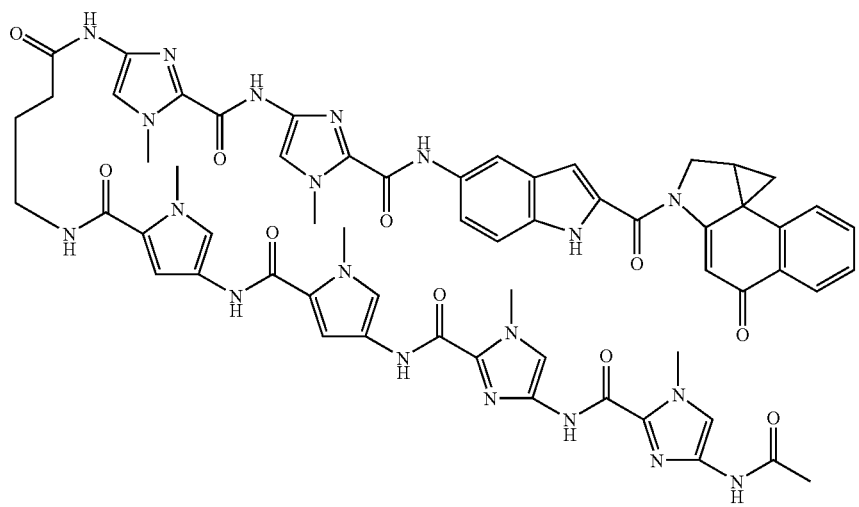

(3-2)

reaction conditions:
(a) HATU, $^{i}Pr_2$ NEt, DMF; (b) (3-2-3), $^{i}Pr_2$ NEt, DMF;
(c) (3-1-5), EDCl, NaHCO$_3$, DMF; (d) 5% aq. NaHCO$_3$ A DNA-alkylating agent of the present invention is composed of the inventive indole derivative represented by general formula (1).

The indole derivative of the present invention used as the alkylating agent may have a hairpin structure to recognize DNA. Alternatively, the indole derivative may dimerize to recognize DNA.

In addition to the hairpin structure and the dimerization, DNA may be recognized by adding a compound having one divalent constitutional unit or having two or more constitutional units which may be the same or different, the constitutional unit being represented by the following formula:

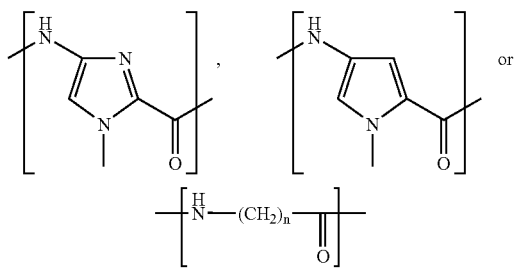

(wherein n is an integer of 0 to 10), wherein among the constitutional units, a terminal constitutional unit adjacent to an N-terminus may be a constitutional unit represented by the following formula:

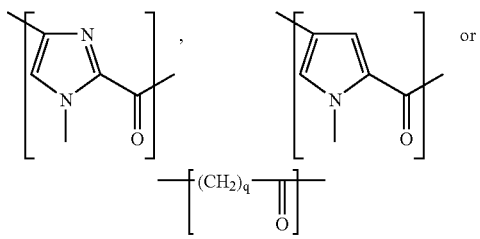

(wherein q is an integer of 0 to 10). That is, a base pair may be recognized by pairing the compound with different indole derivative (1) of the present invention. Furthermore, a base pair may be recognized by pairing the compound with a known minor-groove binder.

A drug of the present invention contains the alkylating agent of the present invention and thus suppresses or activates the expression of a gene.

Examples of the gene suppressed or regulated include abnormal genes, single nucleotide polymorphisms (SNPs), and oncogenes. The inventive indole derivative used as an active component compound of the drug of the present invention may be a pharmaceutically acceptable salt thereof. Examples of the salt include commonly used salts, such as salts with acids, e.g., hydrochlorides, phosphates, citrates, and sulfonates, and salts with organic bases, e.g., methylamine and ethylenediamine.

The indole derivative or the pharmaceutically acceptable salt thereof has advantages described as follows:

(a) the effect of the compound can be expected in a small amount because of high uptake by cancer cells;

(b) the compound can be expected to be orally absorbed because the compound is stable in an acid or an alkali;

(c) it is possible to control the expression of a specific gene; and (d) no damage to normal cells is caused compared with known DNA alkylating agents.

The drug of the present invention is expected to have a therapeutic effect on various diseases by controlling the expression of a gene. In particular, the drug is useful for the treatment and prevention of cancer and can be used for deep cancer. When the drug is used as an anticancer agent, the drug is formed into a commonly used formulation, such as an injection, a tablet, a powder, or a capsule. In making the formulation, a commonly used, pharmaceutically acceptable carrier, such as a binder, a lubricant, a disintegrator, a solvent, a dispersant, a stabilizer, a pigment, or a flavor, may be used. The content of the indole derivative in the formulation is different depending on types of indole derivative and formulation and is usually 0.2 to 50 percent by weight.

The dosage of the inventive drug as an anticancer agent is different depending on age, weight, pathology, a therapeutic effect, an administration method, administration timing, dosing days, and the duration of drug administration. Usually, 10 to 400 mg of the drug is administered once a day for 1, 2, or 3 weeks and 1 week following drug withdrawal as one course of treatment. The administration is repeated. Furthermore, by changing the configuration of imidazole, pyrrole, the β-linker, and the like, the drug can be applied to various types of cancer. Moreover, the drug is used for cancer that causes further expression of abnormal genes. In particular, the drug is used for abnormality of the genes in cancer on which a known anticancer agent does not easily exert an effect.

EXAMPLES

While the present invention will be specifically described by examples, the present invention is not limited to these examples.

Synthesis Example 1 and 2

Synthesis of Compounds (4-1) and (3-1) (Scheme 1)

(1) Synthesis of AcImImCO$_2$H (3-1-1)

Compound (3-1-1) was synthesized according to a method described in literature [(a) Tao, Z.-F.; Fujiwara, T.; Saito, I.; Sugiyama, H. J. Am. Chem. Soc. 1999, 121, 4961. (b) Tao, Z.-F.; Saito, I.; Sugiyama, H. J. Am. Chem. Soc. 2000, 122, 1602. (c) Bando, T.; Narita, A.; Saito, I.; Sugiyama, H. Chem. Eur. J. 2002, 8, 4781].

$^1$H-NMR (500 MHz, DMSO-d$_6$) δ: 10.37 (s, 1H; NH), 9.60 (s, 1H; NH), 7.63 (s, 1H; CH), 7.48 (s, 1H; CH), 3.96 (s, 3H; NCH$_3$), 3.93 (s, 3H; NCH$_3$), 2.03 (s, 3H; COCH$_3$);

ESIMS m/e calcd. for C$_{12}$H$_{15}$N$_6$O$_4$

[M$^+$+H] 307.1. found 307.3.

(2) Synthesis of H$_2$N-Indole-CO$_2$Et (3-1-2)

Compound (3-1-2) was synthesized from commercially available 5-nitroindole-2-carboxylic acid ethyl ester as a starting material by catalytic reduction with Pd—C in a hydrogen atmosphere. Compound (3-1-2) was used as a starting material for synthesizing compound (3-1-3) without purification.

(3) Synthesis of AcImIm-Indole-CO$_2$Et (3-1-3)

Compound (3-1-1) (305 mg, 1.05 mmol) and compound (3-1-2) (215 mg, 1.05 mmol) were dissolved in DMF (2 mL). Then, $^i$Pr$_2$NEt (550 μL, 3.15 mmol) and HATU (480 mg, 1.26 mmol) were added to the resulting solution. The resulting mixture was stirred at room temperature for 15 hours in a nitrogen atmosphere. After completion of the reaction, the solvent in the reaction solution was distilled off under reduced pressure. The resulting residue was purified by silica-gel column chromatography (3% to 5% MeOH in CH$_2$Cl$_2$, gradient elution), followed by removing the solvent to yield a yellow powder (3-1-3) (326 mg, 52%).

$^1$H-NMR (500 MHz, DMSO-d$_6$) δ: 11.83 (s, 1H; NH), 10.32 (s, 1H; NH), 10.08 (s, 1H; NH), 9.40 (s, 1H; NH), 8.16 (s, 1H; CH), 7.60 (s, 1H; CH), 7.56 (d, 1H, J=9.0 Hz; CH), 7.50 (s, 1H; CH), 7.40 (d, 1H, J=9.0 Hz; CH), 7.12 (s, 1H; CH), 4.33 (q, 2H, J=7.0 Hz; OCH$_2$), 4.01 (s, 3H; NCH$_3$), 3.98 (s, 3H; NCH$_3$), 2.03 (s, 3H; COCH$_3$), 1.33 (t, 3H, J=7.0 Hz; CH$_3$);

ESIMS m/e calcd. for C$_{23}$H$_{25}$N$_8$O$_5$

[M$^+$+H] 493.2. found 493.2.

(4) Synthesis of AcImIm-Indole-CO$_2$H (3-1-4)

MeOH (8 mL) and 1 N aqueous sodium hydroxide solution (8 mL) were added to compound (3-1-3) (326 mg, 0.66 mmol). The resulting mixture was stirred at room temperature for 30 minutes. After removal of MeOH under reduced pressure, 10% aqueous HCl solution was added thereto at 0° C. to make the mixture acidic (pH=2). The resulting precipitate was collected by filtration with a KIRIYAMA funnel, washed with water, and dried to yield compound (3-1-4) (297 mg, 96%).

$^1$H-NMR (500 MHz, DMSO-$d_6$) δ: 11.71 (s, 1H; NH), 10.35 (s, 1H; NH), 10.08 (s, 1H; NH), 9.49 (s, 1H; NH), 8.13 (d, 1H, J=1.0 Hz; CH), 7.60 (s, 1H; CH), 7.54 (dd, 1H, J=2.0 and 9.0 Hz; CH), 7.49 (s, 1H; CH), 7.38 (d, 1H, J=9.0 Hz; CH), 7.06 (d, 1H, J=2.0 Hz; CH), 4.01 (s, 3H; NCH$_3$), 3.97 (s, 3H; NCH$_3$), 2.03 (s, 3H; COCH$_3$);

ESIMS m/e calcd. for $C_{21}H_{21}N_8O_5$
[M$^+$+H] 465.2. found 465.2.

(5) Synthesis of seco-CBI (3-1-5)

Compound (3-1-5) was synthesized as a hydrochloride according to a method described in literature [(a) Boger, D. L.; Yun, W. Y.; Teegarden, B. R. J. Org. Chem. 1992, 57, 2873. (b) Boger, D. L.; McKie, J. A. J. Org. Chem. 1995, 60, 1271. (c) Boger, D. L.; Ishizaki, T.; Kitos, P. A.; Suntornwat, O. J. Org. Chem. 1990, 55, 5823]. Spectrum data were reported in the literature.

(6) Synthesis of AcImIm-Indole-seco-CBI (4-1)

seco-CBI (3-1-5) (32.7 mg, 0.13 mmol), EDCI (50.3 mg, 0.26 mmol), and NaHCO$_3$ (41.9 mg, 0.52 mmol) were charged into a reaction vessel containing compound (3-1-4) (60.3 mg, 0.13 mmol). The resulting mixture was dissolved in DMF (700 µL) and stirred at room temperature for 8 hours in a nitrogen atmosphere. After confirmation of completion of the reaction, the solvent was distilled off. The resulting residue was purified by silica-gel column chromatography (5% to 10% MeOH in CH$_2$Cl$_2$, gradient elution). The resulting solid was washed with CHCl$_3$ and dried to yield a brown powder (4-1) (85.2 mg, 96%).

$^1$H-NMR (500 MHz, DMSO-$d_6$) δ: 11.71 (s, 1H; NH), 10.43 (s, 1H; OH), 10.34 (s, 1H; NH), 10.11 (s, 1H; NH), 9.41 (s, 1H; NH), 8.16 (s, 1H; CH), 8.12 (d, 1H, J=8.0 Hz; CH), 7.97 (brs, 1H; CH), 7.85 (d, 1H, J=8.0 Hz; CH), 7.62 (m, 1H; CH), 7.61 (s, 1H; Im-H), 7.52 (t, 1H, J=8.0 Hz; CH), 7.51 (s, 1H; Im-H), 7.45 (d, 1H, J=9.0 Hz; CH), 7.36 (t, 1H, J=8.0 Hz; CH), 7.19 (s, 1H; CH), 4.81 (t, 1H, J=11.0 Hz; NCHH), 4.56 (d, 1H, J=11.0 Hz; NCHH), 4.23 (brt, 1H; CH), 4.03 (s, 3H; NCH$_3$), 3.99 (s, 3H; NCH$_3$), 3.87 (dd, 2H, J=7.0 and 11.0 Hz; CH$_2$), 2.04 (s, 3H; COCH$_3$);

ESI-TOFMS m/e calcd. for $C_{34}H_{31}ClN_9O_5$
[M$^+$+H] 680.22. found 680.23.

(7) Synthesis of AcImIm-Indole-CBI (3-1)

First, 5% aqueous NaHCO$_3$ (100 µL) was added to a solution of compound (4-1) (6.3 mg, 9.28 mmol) in DMF (150 µL). The resulting mixture was stirred at room temperature for 1 hour in a nitrogen atmosphere. After confirmation of completion of the reaction, the solvent was distilled off. The resulting residue was purified by silica-gel column chromatography (5% to 15% MeOH in CH$_2$Cl$_2$, gradient elution). The solvent was distilled off. The resulting residue was dried to yield a brown powder (3-1) (6.0 mg, quant.).

$^1$H-NMR (500 MHz, DMSO-$d_6$) δ: 11.85 (s, 1H; NH), 10.35 (s, 1H; NH), 10.16 (s, 1H; NH), 9.41 (s, 1H; NH), 8.17 (s, 1H; CH), 8.00 (d, 1H, J=8.0 Hz; CH), 7.94 (s, 1H; CH), 7.62 (s, 1H; Im-H), 7.52 (m, 2H; CH×2), 7.51 (s, 1H; Im-H), 7.43 (m, 2H; CH), 7.25 (d, 1H, J=8.0 Hz; CH), 6.95 (s, 1H; CH), 4.64 (m, 1H; NCHH), 4.49 (d, 1H, J=10.0 Hz; NCHH), 4.02 (s, 3H; NCH$_3$), 3.98 (s, 3H; NCH$_3$), 3.27 (brt, 1H; CH), 2.03 (s, 3H; COCH$_3$), 1.75 (m, 1H; CHH), 1.70 (m, 1H; CHH);

ESI-TOFMS m/e calcd. for $C_{34}H_{30}N_9O_5$
[M$^+$+H] 644.23. found 644.21.

Synthesis Example 3

Synthetic Reaction of Compound (3-2) (Scheme 2)

(1) Synthesis of AcImImPyPy-γ-ImPyCO$_2$H (3-2-1)

Compound (3-2-1) was prepared by an Fmoc solid-phase synthesizer. Purification was performed by HPLC with a Chemcobond 5-ODS-H column (conditions: linear gradient of 0-500 acetonitrile in 0.1% acetic acid, 40 min, 254 nm). The resulting compound was used as a starting material for synthesis.

$^1$H-NMR (500 MHz, DMSO-$d_6$) δ: 10.32 (s, 1H; NH), 10.29 (s, 1H; NH), 10.23 (s, 1H; NH), 10.00 (s, 1H; NH), 9.91 (s, 1H; NH), 9.32 (s, 1H; NH), 8.02 (s, 1H; NH), 7.56 (s, 1H; Im-H), 7.50 (s, 1H; Im-H), 7.45 (s, 1H; Py-H), 7.44 (s, 1H; Im-H), 7.27 (s, 1H; Py-H), 7.16 (s, 1H; Py-H), 7.14 (s, 1H; Py-H), 6.92 (s, 1H; Py-H), 6.89 (s, 1H; Py-H), 4.00 (s, 3H; NCH$_3$), 3.97 (s, 3H; NCH$_3$), 3.93 (s, 3H; NCH$_3$), 3.84 (s, 3H; NCH$_3$), 3.81 (s, 3H; NCH$_3$), 3.79 (s, 3H; NCH$_3$), 3.19 (m, 2H; CH$_2$), 2.34 (m, 2H; CH$_2$), 2.03 (s, 3H; COCH$_3$), 1.78 (m, 2H; CH$_2$);

ESI-TOFMS m/e calcd. for $C_{39}H_{45}N_{16}O_9$
[M$^+$+H] 881.35. found 881.36.

(2) Synthesis of H$_2$N-Indole-CO$_2$H (3-2-3)

Compound (3-2-3) was synthesized from commercially available 5-nitroindole-2-carboxylic acid ethyl ester as a starting material by a two-step reaction ((i) alkali hydrolysis with 1 N NaOH; and (ii) catalytic reduction with Pd—C in a hydrogen atmosphere).

$^1$H-NMR (500 MHz, DMSO-$d_6$) δ: 11.22 (s, 1H; NH), 7.11 (d, 1H, J=8.5 Hz; CH), 6.75 (d, 1H, J=2.0 Hz; CH), 6.67 (s, 1H; CH), 6.65 (dd, 1H, J=2.0 and 8.5 Hz; CH), 3.31 (brs, 2H; NH$_2$, H$_2$O)

(3) Synthesis of AcImImPyPy-γ-ImPy-Indole-CO$_2$H (3-2-4)

Compound (3-2-1) (3.5 mg, 3.98 mmol) prepared by a solid-phase synthesis was dissolved in DMF (75 µL). Then, $^i$Pr$_2$NEt (1.4 µL, 8.04 mmol) and HATU (1.4 mg, 3.68 mmol) were added to the resulting solution. The resulting mixture was stirred at room temperature for 4 hours in a nitrogen atmosphere. After confirmation of completion of the reaction, compound (3-2-3) (1.3 mg, 7.38 mmol) and $^i$Pr$_2$NEt (1.3 µL, 7.46 mmol) were added thereto. The resulting mixture was stirred overnight at room temperature in a nitrogen atmosphere. After the reaction, the solvent in the reaction solution was distilled off. The residue was filtrated using a KIRIYAMA funnel and washed with CH$_2$Cl$_2$ and H$_2$O. As a result, crude crystals of compound (3-2-4) were produced (3.0 mg, 73%).

$^1$H-NMR (500 MHz, DMSO-$d_6$) δ: 11.33 (brs, 1H; NH), 10.34 (s, 1H; NH), 10.33 (s, 1H; NH), 10.27 (s, 1H; NH), 9.92 (s, 2H; NH), 9.73 (s, 1H; NH), 9.32 (brs, 1H; NH), 8.01 (brt, 1H; NH), 7.94 (s, 1H; CH), 7.56 (s, 1H; Im-H), 7.50 (s, 1H; Im-H), 7.46 (s, 1H; Im-H), 7.40 (brd, 1H, J=8.5 Hz; CH), 7.31 (brd, 1H, J=8.5 Hz; CH), 7.30 (d, 1H, J=1.5 Hz; Py-H), 7.26

(d, 1H, J=1.5 Hz; Py-H), 7.17 (d, 1H, J=1.5 Hz; Py-H), 7.16 (s, 2H; γ-H×2), 6.90 (d, 1H, J=1.5 Hz; Py-H), 6.85 (brs, 1H; CH), 4.00 (s, 3H; NCH$_3$), 3.97 (s, 3H; NCH$_3$), 3.95 (s, 3H; NCH$_3$), 3.85 (s, 3H; NCH$_3$), 3.84 (s, 3H; NCH$_3$), 3.80 (s, 3H; NCH$_3$), 3.20 (dt, 2H, J=6.0 and 7.5 Hz; CH$_2$), 2.36 (t, 2H, J=7.5 Hz; CH$_2$), 2.04 (s, 3H; COCH$_3$), 1.79 (qu, 2H, J=7.5 Hz; CH$_2$);

ESI-TOFMS m/e calcd. for C$_{48}$H$_{51}$N$_{18}$O$_{10}$
[M$^+$+H] 1039.40. found 1039.39.

(4) Synthesis of AcImImPyPy-γ-ImPy-Indole-CBI (3-2)

Into a reaction vessel containing the crude crystals of compound (3-2-4) (3.0 mg, 2.89 mmol), seco-CBI (3-1-5) (1.4 mg, 6.01 mmol), EDCI (1.2 mg, 6.25 mmol), and NaHCO$_3$ (1.0 mg, 12.0 mmol) were charged. The resulting mixture was dissolved in DMF (100 μL), and the resulting solution was stirred at room temperature for 2 hours in a nitrogen atmosphere. After confirmation of completion of the reaction, 5% NaHCO$_3$ (300 μL) and DMF (300 μL) were added thereto. The resulting mixture was stirred for 30 minutes. After completion of the reaction, the solvent was distilled off. The resulting residue was purified by silica-gel column chromatography (5% to 15% MeOH in CH$_2$Cl$_2$, gradient elution). The solvent was distilled off to yield crude crystals (3-2) (1.33 mg, 27% for 2 steps). Furthermore, purification was performed by HPLC (linear gradient of 0-50% acetonitrile in 0.1% acetic acid, 40 min, 254 nm). The resulting solution was subjected to vacuum concentration and lyophilization to yield yellow crystals (3-2) (0.5 mg, 0.41 μmol; 11% for 2 steps).

$^1$H-NMR (500 MHz, DMSO-d$_6$) δ: 11.77 (s, 1H; NH), 10.32 (s, 1H; NH), 10.29 (s, 1H; NH), 10.26 (s, 1H; NH), 9.95 (s, 1H; NH), 9.92 (s, 1H; NH), 9.82 (s, 1H; NH), 9.33 (s, 1H; NH), 8.08 (s, 1H; CH), 8.01 (brs, 1H; NH), 8.00 (d, J=7.5 Hz, 1H; CH), 7.60 (t, J=7.5 Hz, 1H; CH), 7.56 (s, 1H; CH), 7.53 (d, J=8.5 Hz, 1H; CH), 7.50 (s, 1H; CH), 7.46 (s, 1H; CH), 7.43 (t, J=7.5 Hz, 1H; CH), 7.42 (s, 1H; CH), 7.31 (s, 1H; CH), 7.27 (s, 1H; CH), 7.24 (d, J=8.5 Hz, 1H; CH), 7.22 (s, 1H; CH), 7.19 (s, 1H; CH), 7.16 (d, J=7.5 Hz, 1H; CH), 7.06 (s, 1H; CH), 6.95 (s, 1H; CH), 6.89 (s, 1H; CH), 4.62 (dd, J=10.0 and 5.0 Hz, 1H; NCH$_2$), 4.48 (d, J=10.0 Hz, 1H; NCH$_2$), 4.00 (s, 3H; NCH$_3$), 3.97 (s, 3H; NCH$_3$), 3.95 (s, 3H; NCH$_3$), 3.86 (s, 3H; NCH$_3$), 3.84 (s, 3H; NCH$_3$), 3.80 (s, 3H; NCH$_3$), 3.20 (m, 2H; CH$_2$), 2.90 (m, 1H; CH), 2.35 (m, 2H; CH$_2$), 2.03 (s, 3H; COCH$_3$), 1.79 (m, 2H; CH$_2$), 1.76 (dd, J=7.5 and 5.0 Hz, 1H; CH), 1.70 (t, J=5.0 Hz, 1H; CH);

ESI-TOFMS m/e calcd. for C$_{61}$H$_{60}$N$_{19}$O$_{10}$
[M$^+$+H] 1218.48. found 1218.48.

To synthesize AcImImPyPy-γ-ImPy-Indole-seco-CBI (4-2), after completion of the reaction, the solvent is distilled off without treatment with 5% NaHCO$_3$. The resulting residue is purified by silica-gel column chromatography (5% to 15% MeOH in CH$_2$Cl$_2$, gradient elution) and HPLC (linear gradient of 0-100% acetonitrile in 0.1% acetic acid, 20 min, 254 nm). The resulting solution is subjected to vacuum condensation and lyophilization to yield yellow crystals (4-2).

ESI-TOFMS m/e calcd. for C$_{61}$H$_{61}$ClN$_{19}$O$_{10}$
[M$^+$+H] 1254.45. found 1254.50.

Synthesis Example 4

Synthesis of AcImImPy-γ-Im-Indole-CBI (3-3)

Compound (3-3) was synthesized in the same synthetic procedure as that in Synthesis Example 3. Purification was performed by HPLC with a Chemcobond 5-ODS-H column (conditions: linear gradient of 0-50% acetonitrile in 0.1% acetic acid, 40 min, 254 nm). The resulting compound was used for a DNA-alkylating reaction.

ESI-TOFMS m/e calcd. for C$_{49}$H$_{48}$N$_{15}$O$_{8}$
[M$^+$+H] 974.37. found 974.26.

Synthesis Example 5

Synthesis of AcImImPyPy-γ-PyPy-Indole-CBI (3-4)

Compound (3-4) was synthesized in the same synthetic procedure as that in Synthesis Example 3. Purification was performed by HPLC with a Chemcobond 5-ODS-H column (conditions: linear gradient of 0-50% acetonitrile in 0.1% acetic acid, 40 min, 254 nm). The resulting compound was used for a DNA-alkylating reaction.

ESI MS m/e calcd. for C$_{62}$H$_{61}$N$_{18}$O$_{10}$
[M$^+$+H] 1217.5. found 1217.4.

Synthesis Example 6

Synthesis of AcImPyPyPy-γ-ImPy-Indole-CBI (3-5)

Compound (3-5) was synthesized in the same synthetic procedure as that in Synthesis Example 3. Purification was performed by HPLC with a Chemcobond 5-ODS-H column (conditions: linear gradient of 0-50% acetonitrile in 0.1% acetic acid, 40 min, 254 nm). The resulting compound was used for a DNA-alkylating reaction.

ESI-TOFMS m/e calcd. for C$_{62}$H$_{61}$N$_{18}$O$_{10}$
[M$^+$+H] 1217.5. found 1217.4.

Synthesis Example 7

Synthesis of AcImImPyPyβPyPy-γ-ImPyβImPy-Indole-CBI (3-6)

Compound (3-6) was synthesized in the same synthetic procedure as that in Synthesis Example 3. Purification was performed by HPLC with a Chemcobond 5-ODS-H column (conditions: linear gradient of 0-50% acetonitrile in 0.1% acetic acid, 40 min, 254 nm). The resulting compound was used for a DNA-alkylating reaction.

ESI MS m/e calcd. for C$_{90}$H$_{93}$N$_{30}$O$_{16}$
[M$^+$+H] 1849.7. found 1850.1.

Synthesis Example 8

Synthesis of AcImImPy-β-ImPy-Indole-CBI (3-7)

Compound (3-7) was synthesized in the same synthetic procedure as that in Synthesis Example 3. Purification was performed by HPLC with a Chemcobond 5-ODS-H column (conditions: linear gradient of 0-50% acetonitrile in 0.1% acetic acid, 40 min, 254 nm). The resulting compound was used for a DNA-alkylating reaction.

ESI-TOFMS m/e calcd. for C$_{54}$H$_{52}$N$_{17}$O$_{9}$
[M$^+$+H] 1082.5. found 1082.4.

Synthesis Example 9

Synthesis of AcImImIm-γ-PyPy-Indole-seco-CBI (4-3)

Compound (4-3) was synthesized by applying solution-phase synthesis of an already reported Py-Im polyamide. Purification was performed by HPLC with a Chemcobond 5-ODS-H column (conditions: linear gradient of 0-100% acetonitrile in 0.1% acetic acid, 20 min, 254 nm). The resulting compound was used for a DNA-alkylating reaction.

ESI-TOFMS m/e calcd. for C$_{55}$H$_{55}$ClN$_{17}$O$_{9}$
[M$^+$+H] 1132.5. found 1132.4.

Synthesis Example 10

Synthesis of AcImImPyPy-β-PyPyPy-β-Dp (6)

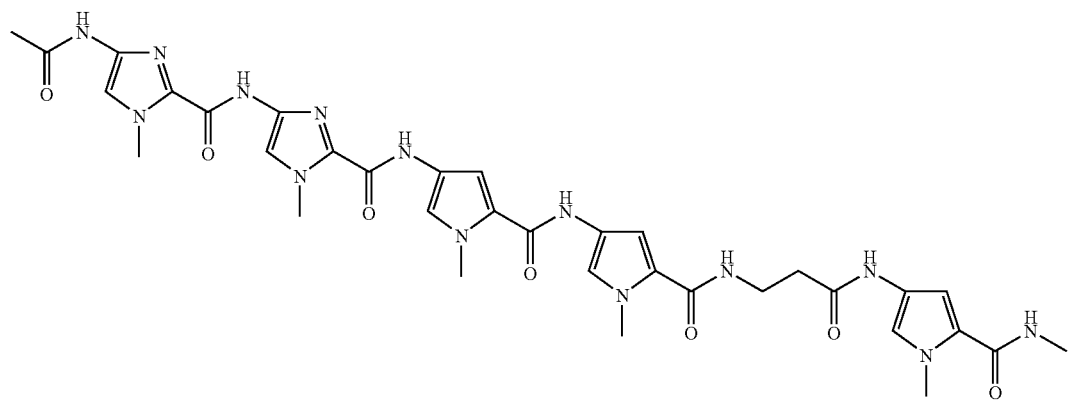

(6)

Compound (6) was synthesized with an fmoc solid-phase synthesizer and separated from a solid-phase support by heating in the presence of dimethylaminopropylamine.

Purification was performed by HPLC with a Chemcobond 5-ODS-H column (conditions: linear gradient of 0-100% acetonitrile in 0.1% acetic acid, 20 min, 254 nm).

ESI-MS m/e calcd. for $C_{53}H_{67}N_{20}O_{10}$
[M$^+$+H] 1143.9. found 1143.5.

In each of Synthesis Examples 1 to 10 described above, reagents, such as N,N-diisopropylethylamine ($^iPr_2NEt$) and O-(7-azabenzotriazole-1-yl)-1,1,3,3-tetramethyluronium (HATU), solvents, such as N,N-dimethylformamide (DMF), and the like were mainly purchased from a reagent manufacturer, such as Sigma-Aldrich Co., and used without purification. Unless otherwise specified, the reaction was monitored by high-performance liquid chromatography (HPLC) at a UV wavelength of 254 nm UV. The $^1$H-NMR spectrum was measured with JEOL JNM-A 500 (500 MHz) using tetramethylsilane (TMS) as an internal standard. With respect to multiplicity, a singlet, a doublet, a triplet, a quartet, a quintet, a multiplet, and broad were abbreviated as s, d, t, q, qu, m, and br, respectively. Electrospray ionization mass spectra (ES-IMS) were measured with a PE SCIEX API 165. Electrospray ionization time-of-flight mass spectrometry (ESI-TOFMS) was performed on a BioTOFII (Bruker Daltonics) mass spectrometer. Polyacrylamide gel electrophoresis was performed on a HITACHI 5500-S DNA Sequencer. The loading dye (dimethylformamide with fushin red) was purchased from Amersham Co. Ltd., and 50% Long Ranger™ gel solution was purchased from FMC Bioproducts. Calf intestine alkaline phosphatase (AP, 1,000 unit/mL) was purchased from Boehringer Mannheim.

Synthesis of 5'-Texas Red-Labeled DNA Fragment

A 5'-Texas Red-labeled DNA fragment (450 bp) (pUC-I', SEQ ID NO:1) was prepared by a PCR method using a 5'-Texas Red-labeled 20-base-pair primer, i.e., 5'-TexRed-AGAATCAGGGGATAACGCAG-3' (pUC18 forward, 780-799; SEQ ID NO:2), and a 20-base-pair primer, i.e., 5'-TTAC-CAGTGGCTGCTGCCAG-3' (pUC18 reverse, 1459-1478; SEQ ID NO:3), puc18 being used as a template. The DNA fragment was in a double-stranded state including a complementary strand (the following fragments were in the same state).

A 5'-Texas Red-labeled DNA fragment (450 bp) (pUC-II, SEQ ID NO:4) was prepared by a PCR method using a 5'-Texas Red-labeled 21-base-pair primer, i.e., 5'-TexRed-TGCTGGCCTTTTGCTCACATG-3' (pUC18 reverse, 1861-1881; SEQ ID NO:5), and a 19-base-pair primer, i.e., 5-TG-TAAAACGACGGCCAGTG-3' (pUC18 forward, 328-345; SEQ ID NO:6), puc18 being used as a template.

A 5'-Texas Red-labeled DNA fragment (450 bp) (pUC-II', SEQ ID NO:7) was prepared by a PCR method using the 5'-Texas Red-labeled 19-base-pair primer (pUC18 forward, 328-345; SEQ ID NO:6) and the 21-base-pair primer (pUC18 reverse, 1861-1881; SEQ ID NO:5), puc18 being used as a template.

A 5'-Texas Red-labeled DNA fragment (537 bp) (λ-F10906; SEQ ID NO:8) was prepared by a PCR method using a 5'-Texas Red-labeled 23-base-pair primer, i.e., 5'-TexRed-ATCAGGGCAACTCAACCCTGTCC-3' (λ-DNA forward, 10960-10982; SEQ ID NO:9), and a 20-base-pair primer, i.e., 5'-CAGGACGACCAATATC-CAGC-3' (λ-DNA reverse, 37007-37026; SEQ ID NO:10), λ-DNA being used as a template.

A 5'-Texas Red-labeled DNA fragment (994 bp) (pQBI63; SEQ ID NO:11) was prepared by a PCR method using a 20-base-pair primer, i.e., 5'-GGTGATGTCGGCGATAT-AGG-3' (SEQ ID NO:12), and a 5'-Texas Red-labeled 20-base-pair primer, i.e., 5'-TexRed-CCCCAAGGGGTTAT-GCTAGT-3' (SEQ ID NO:13), pQBI63 plasmid being used as a template.

A 5'-Texas Red-labeled 727-bp DNA fragment (SEQ ID NO:14) was prepared by a PCR method using a 5'-Texas Red-labeled 20-base-pair primer, i.e., 5'-TexRed-CCCAT-TCTAAACTGTACCCT-3' (SEQ ID NO:15), and a 21-base-pair primer, i.e., 5'-GGCATCAAGGAAGGTGATTGG-3' (SEQ ID NO:16), a plasmid containing MLP into which the code base sequence of human β-globin was integrated being used as a template.

A 5'-Texas Red-labeled 446-bp DNA fragment (SEQ ID NO:17 with a 24-times-repeated telomere sequence was prepared by a PCR method using a 5'-Texas Red-labeled 20-base pair primer, i.e., 5'-TexRed-GGCCAGTGAATTG-TAATACG-3' (SEQ ID NO:18), and a 20-base-pair primer, i.e., 5'-CCAGGCTTTACACTTTATGC-3' (SEQ ID NO:19), pCR2.1 plasmid into which an oligomer having a repetitive telomere sequence was integrated from the cleavage site by EcoRI being used as a template. The resulting each DNA fragment was purified by filtration using Suprec-02. The concentration of each resulting product was determined by measuring UV absorption.

Ability to Alkylate Linear DNA (400 by or More)

The reaction of compounds (3-1) and (4-1) prepared in the above-described Synthesis Examples with DNA was studied using the long-chain DNA (pUC-II; SEQ ID NO:7). An alkylation reaction was performed at 23° C. for 8 hours. The sequence alkylated was analyzed by polyacrylic gel electrophoresis for sequence determination. FIG. 1 shows the results. Open-circular compound (4-1) and circular compound (3-1) had the same sequence specificity and was selectively alkylated adenine located at site 1 (5'-CGGCCA-3') at nanomolar concentrations. This sequence specificity can be explained by a model in which each compound dimerizes in the DNA minor groove to recognize the base sequence.

Analysis by polyacrylamide gel electrophoresis was performed by the following process: A standard reaction solution containing the 5'-Texas Red-end-labeled DNA fragment (10 nM), DMF (10% (v/v)), and an agent having a concentration described above in a sodium phosphate buffer (5 mM, total volume: 10 μL, pH=7.0) was charged into a microfuge tube (Eppendorf) and left standing at 23° C. for 8 hours. After completion of the reaction, the reaction was quenched by the addition of calf thymus DNA (1 mM, 1 μL). The resulting mixture was shaken at 90° C. for 5 minutes. The DNA obtained by centrifugation under reduced pressure was dissolved by the addition of 8 μl, of loading dye (fushin red solution in DMF), shaken at 94° C. for 20 minutes, and then immediately cooled to 0° C. A 2-μL aliquot was separated electrophoretically on a 6% denaturing polyacrylamide gel using a Hitachi 5500-S DNA sequencer. The following tests were conducted in a similar way.

Figure 2:
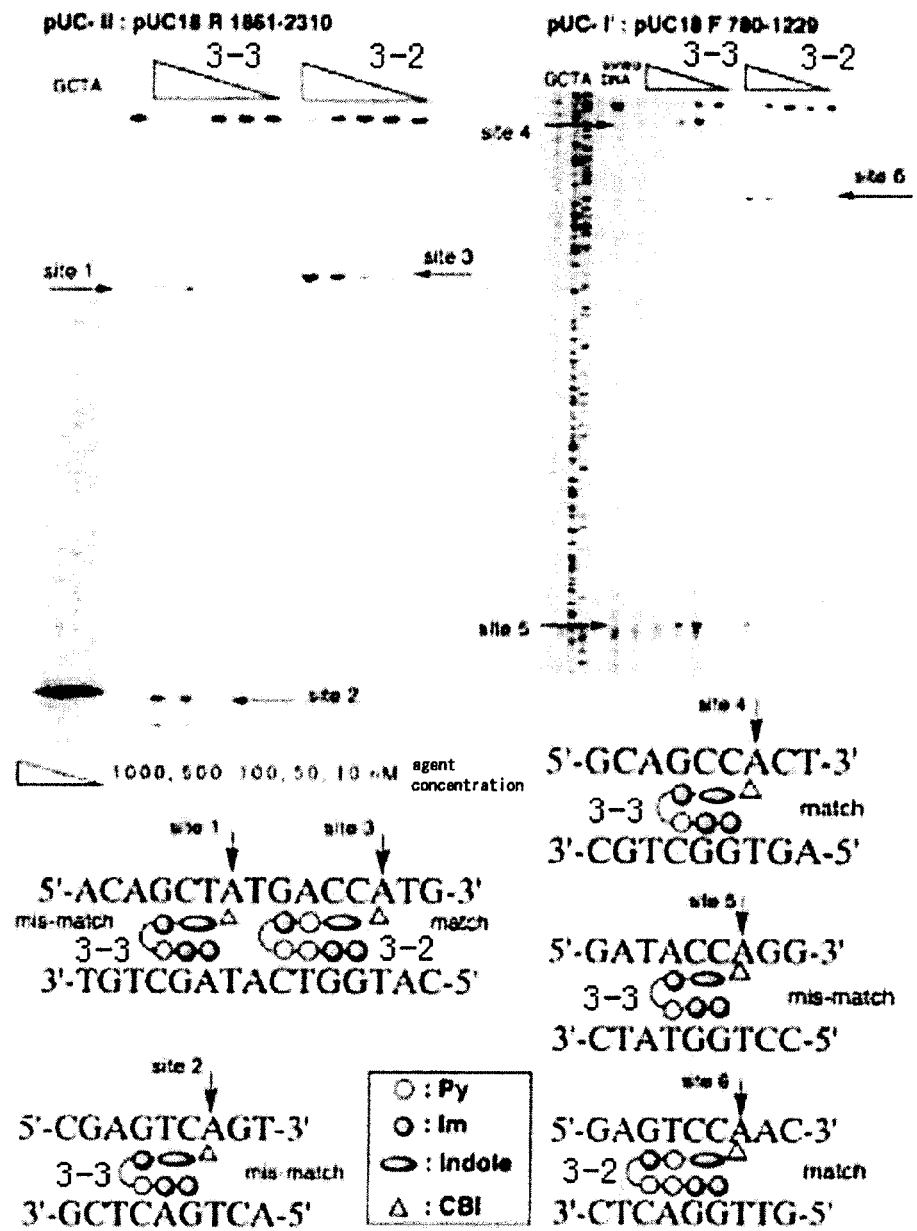
FIG. 2 shows the abilities of compounds (3-2) and (3-3) of the present invention to DNA-sequence-specifically alkylate a long-chain DNA (pUC-II and pUC-I') and sequence recognition models thereof.

The reaction of compounds (3-2) and (3-3) prepared in the above-described Synthesis Examples with DNA was studied using the long-chain DNA (pUC-II; SEQ ID NO:4, pUC-I'; SEQ ID NO:1). An alkylation reaction was performed for 8 hours. The sequence alkylated was analyzed by polyacrylic gel electrophoresis for sequence determination. FIG. 2 shows the results. As a result, in both compounds (3-2) and (3-3), efficient DNA alkylation comparable with that of a known Py-Im polyamide having a vinyl linker was observed at nanomolar concentrations. However, the difference in sequence recognition ability was observed. In compound (3-3), alkylation of site 4 (5'-AGCCA-3'), which was a match sequence, was observed. On the other hand, single-base-pair mismatch sequences in site 1 (5'-AGCTA-3'), site 2 (5'-AGTCA-3'), site 5 (5'-TACCA-3'), and the like were also observed. In contrast, in compound (3-2), alkylation in only site 3 (5'-TGACCA-3') and site 6 (5'-AGTCCA-3'), which were match sequences, was observed. From the stand point of the sequence recognition ability, the molecular design of compound (3-2) was excellent. Interestingly, although pUC-I' (SEQ ID NO:1) contained a site (5'-TGCCG-3') corresponding to a match sequence of compound (3-3), no alkylation of guanine was observed.

Figure 3:
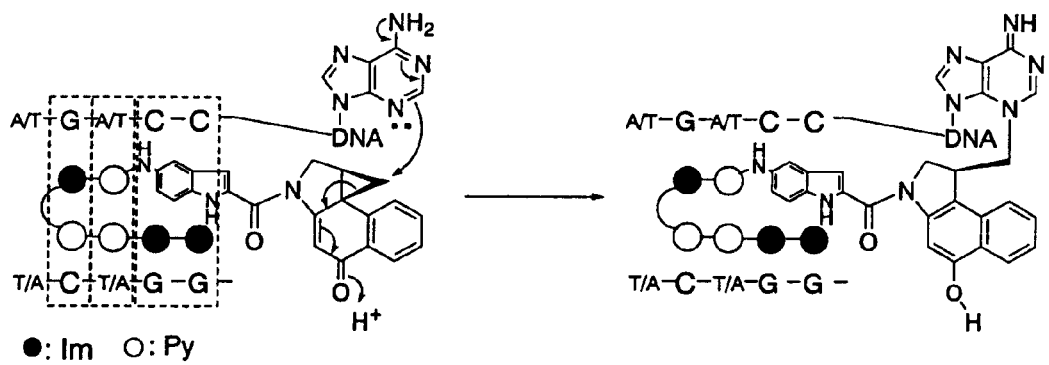
FIG. 3 shows a model of base-sequence-specific alkylation of DNA by compound (3-2) of the present invention.

In consideration of the results shown in FIG. 2, it is believed that the combination of the indole linker and CBI alkylates adenine at the N-3 position with highly sequence specificity. In sequence recognition, it is believed that the indole linker adjusts the distance between the cyclopropane ring of CBI and the N-3 position of adenine so as to cause alkylation while functioning as like Py (FIG. 3).

Figure 4:
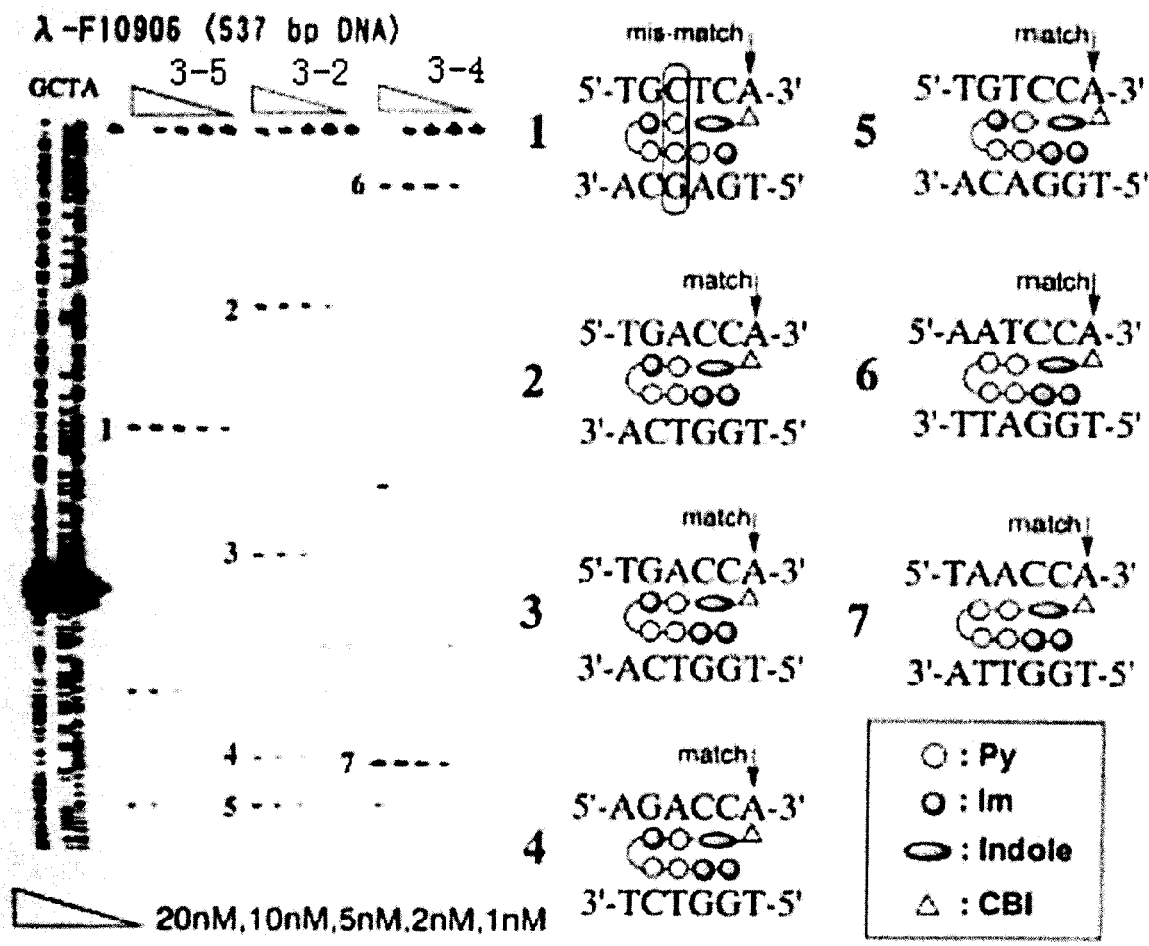
FIG. 4 shows abilities of compounds (3-2), (3-4), and (3-5) of the present invention to DNA-sequence-specifically alkylate a long-chain DNA (λ-F10906); and sequence recognition models thereof.

The reaction of compounds (3-2), (3-4), and (3-5) with DNA was studied using the long-chain DNA (λ-F10906; SEQ ID NO:8). The DNA-alkylating ability of each compound was evaluated. FIG. 4 shows the results. Sequence-specific DNA alkylation (site 2 and 3: 5'-TGACCA-3', site 4: 5'-AGACCA-3', site 5: 5'-TGTCCA-3') by compound (3-2) was observed at nanomolar concentrations as in the results shown in FIG. 2. Furthermore, Sequence-specific DNA alkylation (site 6: 5'-AATCCA-3', site 7: 5'-TAACCA-3') by compound (3-4) was also observed at nanomolar concentrations. In compound (3-5), alkylation of an only mismatch sequence (site 1: 5'-TGCTCA-3') was observed. These results indicate the possibility that in the molecular design of the hairpin Py-Im polyamide including the indole linker, alkylating agents that are capable of recognizing intended sequences can be produced by only changing the configuration of Py-Im.

Figure 5:
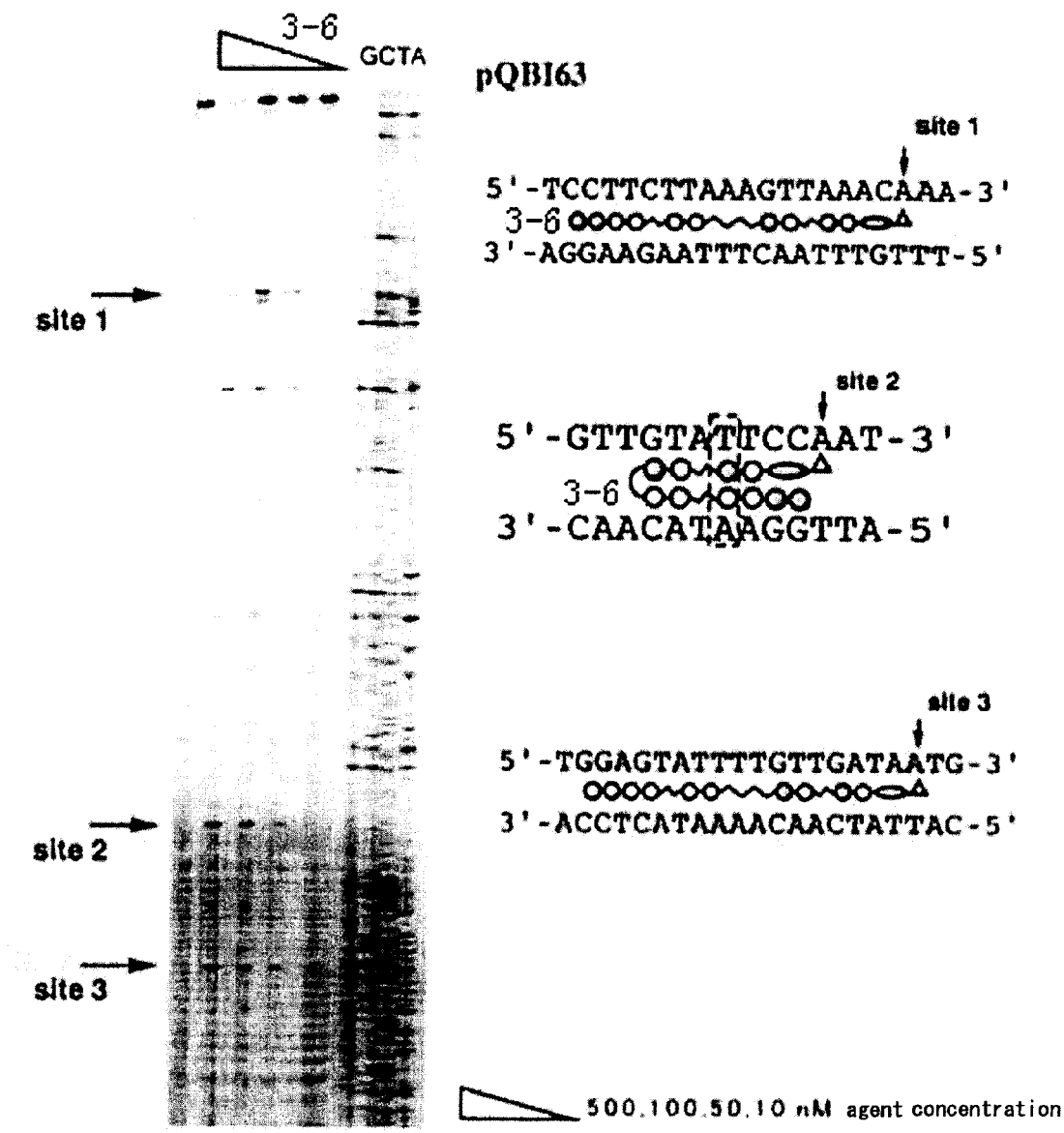
FIG. 5 shows the DNA-sequence-specific alkylation of a long-chain DNA (pQBI63) by compound (3-6) of the present invention.

Establishment of the synthetic pathway using the indole linker made it possible to synthesize an alkylating agent, which cannot be synthesized using a known vinyl linker, having the ability to recognize a longer base sequence. For example, a Py-Im carboxylic acid having the ability to recognize a long base sequence was prepared by Fmoc solid-phase synthesis for a Py-Im polyamide using an oxime resin, thus making it possible to synthesize compound (3-6) shown in Synthesis Example 7. Alkylation of the DNA fragment (SEQ ID NO:11) derived from pQBI63 was studied. The results demonstrated that compound (3-6) efficiently alkylated 1,000-base-pair DNA at nanomolar concentrations (FIG. 5). Furthermore, alkylation (site 2) due to 1-bp-mismatch recognition was observed. However, alkylation of AT-rich base sequences (sites 1 and 3) was also observed. In the Py-Im polyamide, such as compound (3-6), having the ability to recognize a long base sequence, the maintenance of high specificity is an important issue. It is believed that further optimization of the current molecular design makes it possible to produce a practical alkylating agent having the ability to recognize a sequence having 10 base pair or more with excellent versatility.

Stability of Hairpin Polyamide

Analysis of stability under acidic and alkaline conditions by HPLC was performed by the following process: A reaction solution containing compound (3-1) or (4-1) (100 μM) in a total volume of 10 μL of an aqueous solution of 5% HCl (pH=1, DMF:H$_2$O=1:9) or an aqueous solution of 5% NaHCO$_3$ (pH=9, DMF:H$_2$O=1:9) was charged into a microfuge tube (Eppendorf) and left standing at 37° C. After 30 minutes, 2 hours, and 24 hours, analysis of compound (4-1) (16.8 min) and compound (3-1) (15.1 min) was performed by HPLC (linear gradient of acetonitrile 0-100% in 50 mM ammonium formate, 20 min, flow rate: 1.0 mL/min, 254 nm).

Figure 6:
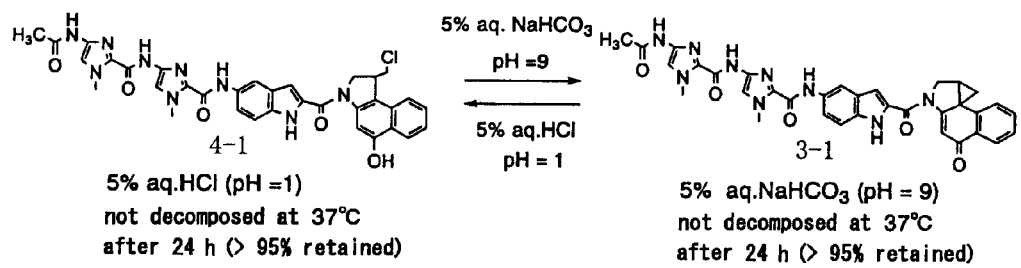
FIG. 6 shows stability of compounds (4-1) and (3-1) of the present invention under acidic and alkaline conditions.

The Py-Im polyamide containing the indole linker was evaluated for stability by product analysis on HPLC using compounds (4-1) and (3-1). FIG. 6 shows the results. It was found that compound (4-1) was not hydrolyzed at all in the acidic aqueous HCl solution (pH=1) (left standing at 37° C. for 24 hours). Compound (4-1) was converted into compound (3-1) (30 minutes: 50%, 2 hours: 78%) in the alkaline aqueous NaHCO$_3$ solution (pH=9) (left standing at 37° C. for 24 hours). No other hydrolysates were formed. Compound (3-1) was readily converted into compound (4-1) (30 minutes: 96%) in the acidic aqueous HCl solution (pH=1) (37° C.). That is, it was found that the Py-Im polyamide containing the indole linker was stably present in a seco-CBI form like compound (4-1) under the acidic condition (pH=1) and in a CBI form like compound (3-1) under the alkaline condition (pH=9).

Sequence-Specific Alkylation of DNA by Polyamide Heterodimer

Figure 7:
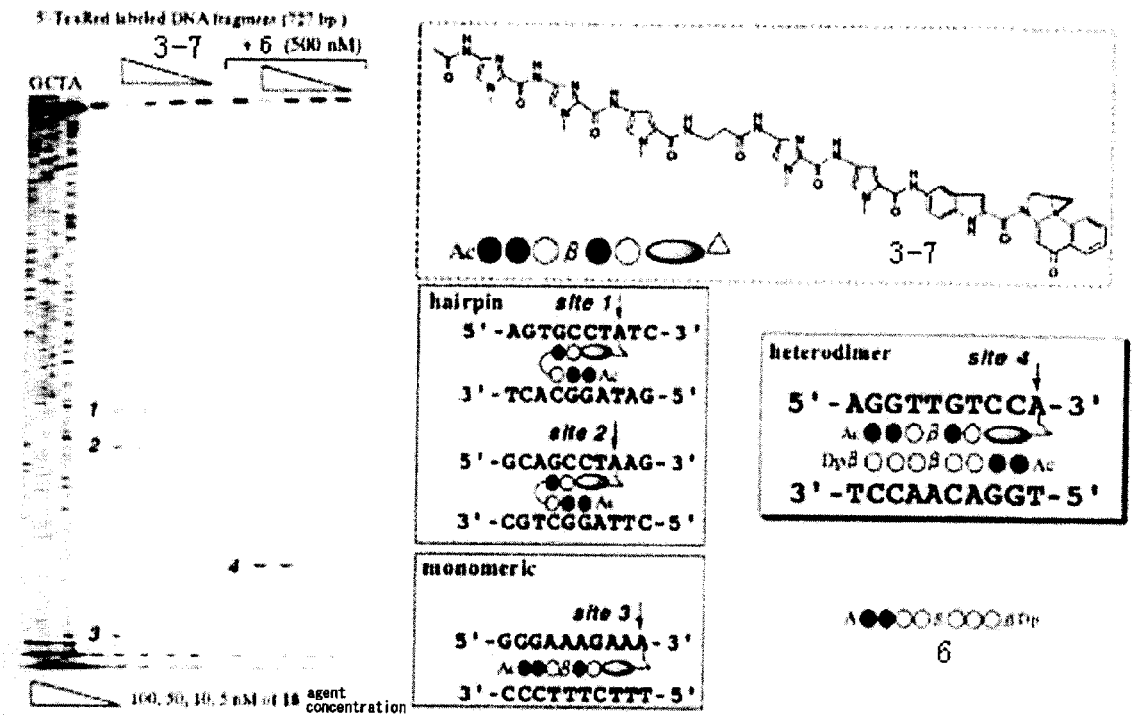
FIG. 7 shows DNA-sequence-specific alkylation of a long-chain DNA (727 bp) by compound (3-7) alone or the combination of compounds (3-7) and (6) of the present invention.

A Py-Im carboxylic acid having the ability to recognize a sequence and a minor-groove binder can be provided by Fmoc solid-phase synthesis for a Py-Im polyamide. Thus, compounds (3-7) and (6) can also be prepared by Fmoc solid-phase synthesis as shown in Synthesis Examples 8 and 10. Alkylation of the 727-bp DNA fragment (SEQ ID NO:14) by compound (3-7) was studied. As a result, efficient alkylation of sites 1 and 2 based on a hairpin mode of recognition and of site 3 based on a linear-chain mode of recognition by compound (3-7) was observed at nanomolar concentrations (FIG. 7). Interestingly, a heterodimer was formed in the presence of compound (6) (500 nM), which was a minor groove binder, and alkylation (site 4) based on accurate 10-base-pair recognition was observed. It was found that the synergetic effect of two molecules of compounds (3-7) and (6) resulted in the ability to recognize a long base sequence. This finding is important in view of the expansion of the recognition by the Py-Im polyamide.

DNA Alkylation Targeting Telomeric Sequence

Figure 8:
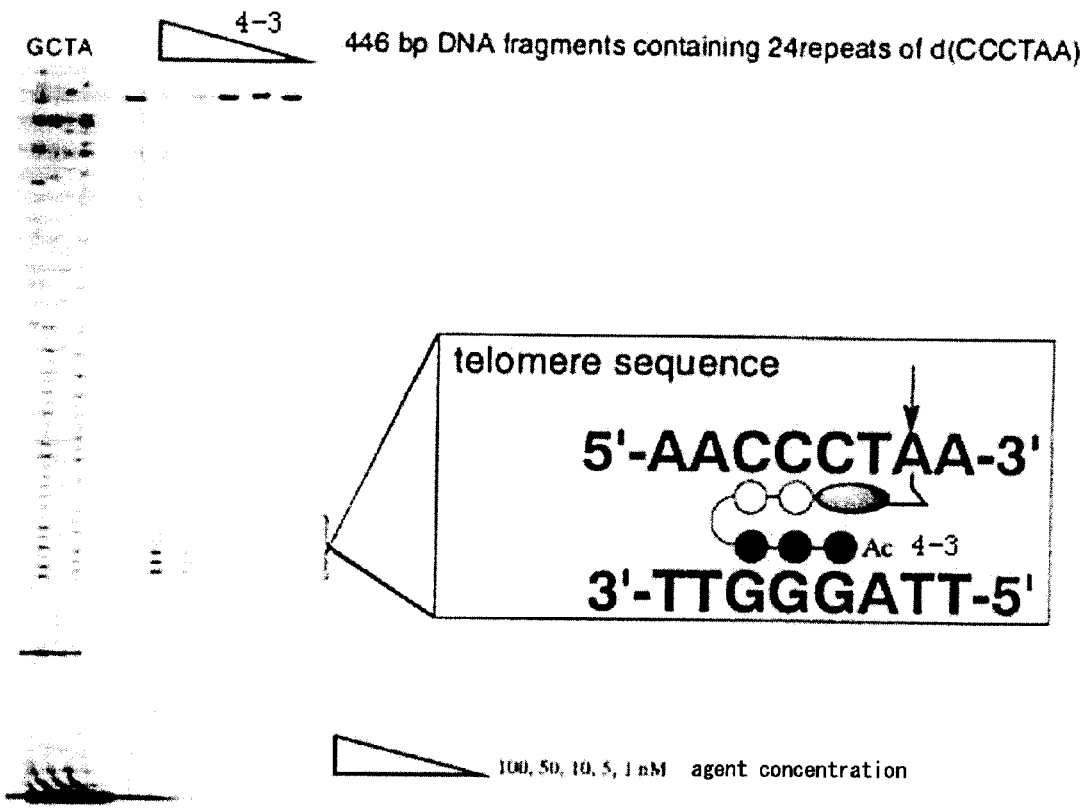
FIG. 8 shows telomere-sequence-specific alkylation of a DNA fragment (446 bp) having 24 repeats of a telomeric sequence by compound (4-3) of the present invention.

A continuous base sequence, i.e., 5'-GGGTTA-3', is present at each terminus of DNA in a cell. It is suggested that the base sequence is greatly associated with growth and replication of cell. Alkylation of the DNA fragment (446 bp; SEQ ID NO:17) containing 24 repeats of a telomeric sequence by compound (4-3) was studied. Efficient telomeric-sequence-specific alkylation (5'-ACCCTA-3') in a hairpin mode of recognition by compound (4-3) was observed at nanomolar concentrations (FIG. 8). An alkylating agent containing the Py-Im polyamide having an indole linker has a high degree of flexibility in molecular design, thereby possibly recognizing various target base sequence.

Anticancer Activity In Vitro by Hairpin Polyamide

Figure 9:
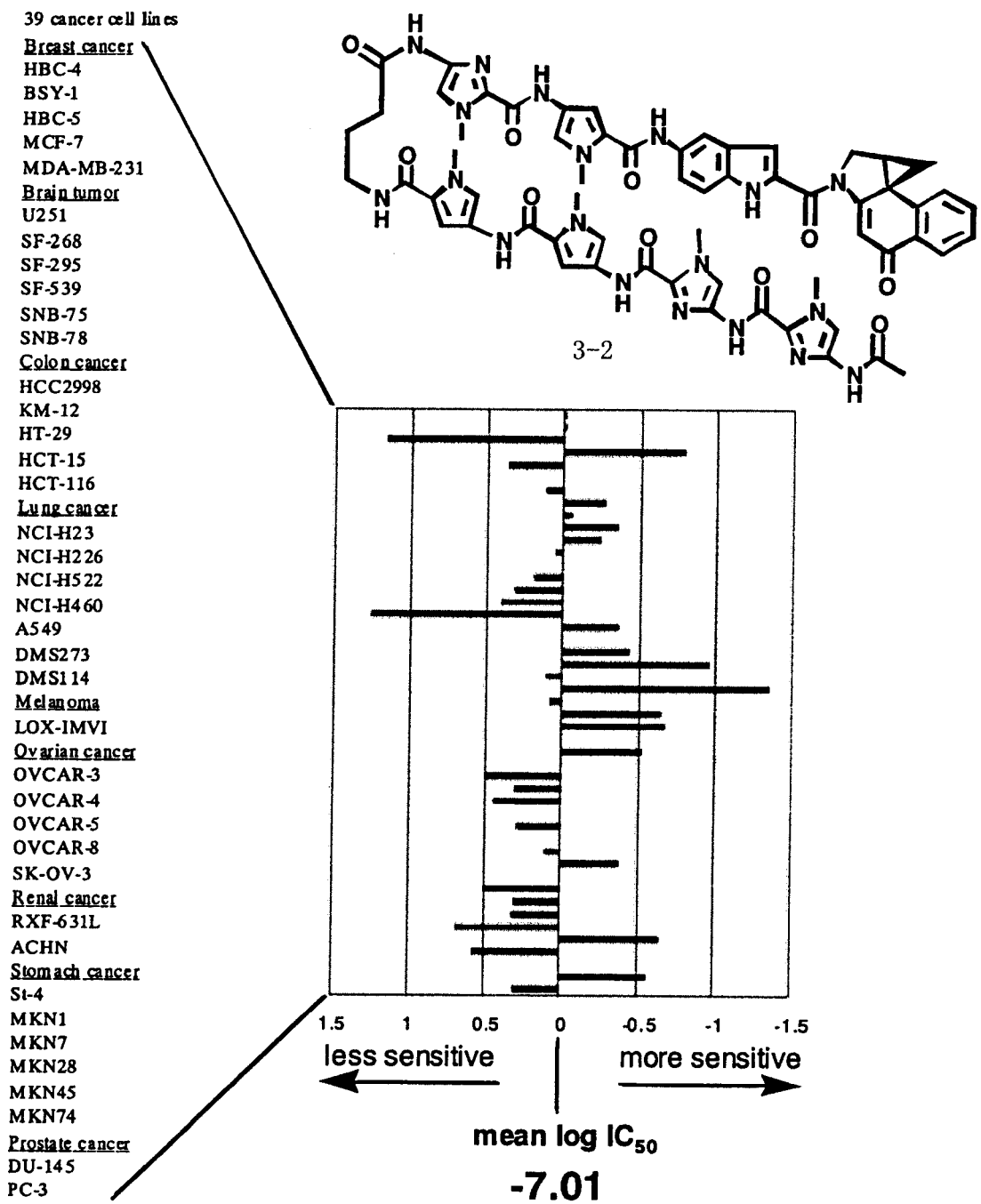
FIG. 9 is a bar graph showing the anticancer activity of inventive compound (3-2) resulting from evaluation on 39 cultured human cancer cell lines, such as breast cancer cell line and prostate cancer cell line.

To examine the activity of the Py-Im polyamide (3-2) containing the indole linker, which showed the most satisfactory sequence-specific alkylation, evaluation was made on 39 cultured human cancer cell lines, such as breast cancer cell line and prostate cancer cell line (FIG. 9). The axis of ordinates of the bar graph shows the 39 cultured human cancer cell lines. The value "0" of the abscissa axis refers to the mean log IC$_{50}$ value. A longer bar extending rightward means that the compound has a higher effect on the corresponding cancer. In contrast, a longer bar extending leftward means that the compound has a lower effect on the corresponding cancer. Compound (3-2) has relatively strong activity against cultured human cancer cells (mean log IC$_{50}$ value of 39 cell lines is about −7 (100 nM)) and thus shows interesting anticancer activity. Evaluation of the anticancer activity on the 39 cultured human cancer cell lines from breast cancer cell line to prostate cancer cell line was made by screening test performed in The Japanese Foundation for Cancer Research.

HCT-116 (human colon cancer-derived cell), HeLa (human cervical cancer-derived cell), HLC-2 (human lung cancer-derived cell), and SH-SY-5Y (human neuroblast-derived cell) were treated with AcImImPyPy-γ-ImPy-Indole-CBI (3-2) ($10^{-5}$ to $10^{-8}$ M with 0.1% DMF) for 48 hours to evaluate the effect of the compound as an anticancer agent. As a result, 50% cell growth inhibitory concentration (IC$_{50}$) against HCT-116, HeLa, HLC-2, and SH-SY-5Y were 7.42× $10^{-8}$, 5.97×$10^{-8}$, 5.35×$10^{-8}$, and 7.43×$10^{-9}$ M, respectively. Similarly, evaluation of 293T (human kidney-derived normal cell) and WI-38 (human normal fibroblast) were made, and IC$_{50}$ was 6.99×$10^{-8}$ and 6.79×$10^{-8}$ M, respectively. The results indicated that the anticancer activity of the compound (3-2) against the cancerous cell lines was about 10 times that against the normal cell lines (IC$_{50}$ values were calculated with reference to a system as a control treated with 0.1% DMF for 48 hours).

Evaluation of anticancer activity was made by the following process: HCT-116, HeLa, HLC-2, and SH-SY-5Y cell lines were seeded into a 96-well flat bottom plate in complete media [RPMI1640 (HCT-116, SH-SY-5Y; Sigma-Aldrich Co.) each containing 10% fetal bovine serum and Dulbecco's modified minimal media (HeLa, HLC-2, 293T, WI-38; Sigma-Aldrich Co.)] at cell densities of 4.0×$10^3$, 3.6×$10^3$, 1.6×$10^3$, 7.0×$10^2$, 5.0×$10^2$, and 8.0×$10^2$ cells/well and were precultured for 24 hours in a CO$_2$ incubator. The media were replaced with complete media containing 0.1% DMF and $10^{-5}$ to $10^{-8}$ M AcImImPyPy-γ-ImPy-Indole-CBI (3-2). Incubation was performed for 48 hours in the CO$_2$ incubator. Then, 10 μL/well of a Cell Counting Kit-8 (Dojindo Laboratories) was added. The specimens were left standing for 2 hours in the CO$_2$ incubator. Absorbance was measured with a microplate reader MPR-A4I (Tosoh Corp.).

Anticancer Activity in vivo of Hairpin Polyamide

Antitumor activity of compound (4-2) against transplantable human ER(+) breast cancer Br-10 in nude mice was studied. Human ER(+) breast cancer Br-10 was subcutaneously transplanted in dorsal portions of 8-week-old BALB/cA-nu/nu mice through a trocar. Injection of 0.1 mL of EP Hormone Depot was intramuscularly administered in Br-10-transplant mice simultaneously with the transplantation. When the tumor volume reached about 100 mm$^3$, the mice were divided into 5 mice/group, and then the administration started.

Compound (4-2) was dissolved in ethanol, diluted with physiological saline, and subcutaneously injected in divided doses into 3 or 4 portions near the tumor once a day and 3 times every 3 days. The dose of compound (4-2) was 50 mg/kg (about 1 mg/mouse) in a volume of 0.05 mL/10 g. Physiological saline was subcutaneously injected in the control group. The length of the major axis (L) and the length of the minor axis (W) were measured every 3 days. The tumor volume was calculated with the following formula:

Tumor volume (mm$^3$)=$L$(mm)×$W^2$(mm$^2$)/2

Comparison of the tumor volume between the compound (4-2) treated group and the control group was performed. Table 1 shows the results. Values shown in the table show relative estimation of each group when the tumor volume after 1 day in each group is defined as 1.0; and relative estimation calculated with (tumor volume of compound (4-2) treated group: T)/(tumor volume of control group: C)×100%.

|  | after 1 day | after 4 days | after 7 days | after 10 days | after 13 days | after 16 days |
| --- | --- | --- | --- | --- | --- | --- |
| control group | 1.0 | 1.4 | 1.7 | 2.1 | 2.7 | 3.1 |
| compound (4-2) | 1.0 | 1.1 | 1.4 | 1.4 | 1.5 | 2.0 |
| T/C (%) | 100 | 78.6 | 82.4 | 66.7 | 55.6 | 64.5 |

From Table 1, in the group in which subcutaneous injection of compound (4-2) was performed, the suppression of tumor growth was observed after the first administration. The subsequent administration showed further significant suppression of the tumor growth. In this experiment, toxicity that causes the weight loss of mice and the like was not observed.

The invention claimed is:

1. An indole derivative represented by general formula (1):

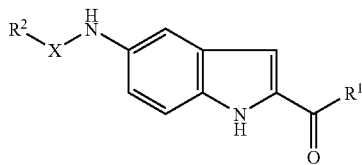
(1)

wherein $R^1$ represents by the following formula:

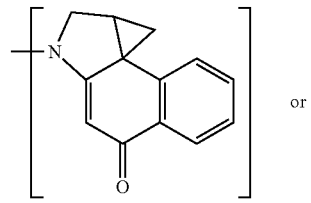
(3)

or

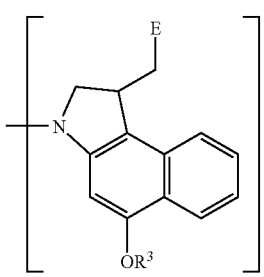
(4)

(wherein in formula (4), $R^3$ represents a hydrogen atom, a peptide chain, a carbohydrate chain, or a polyethylene glycol group; and E represents an elimination group selected from the group consisting of a halogen atom, a mesyl group, and a tosyl group); $R^2$ represents a hydrogen atom, an alkyl group, or an acyl group; and X represents a divalent group having two or more constitutional units which may be the same or different, the constitutional unit being represented by the following formula:

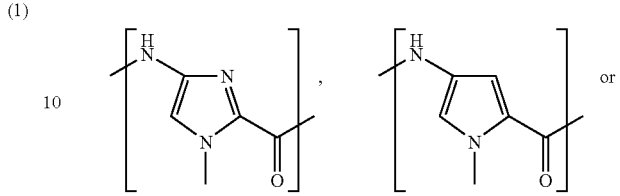

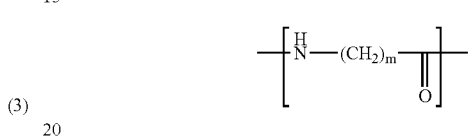

(wherein m is an integer of 0 to 10), wherein among the constitutional units, a terminal constitutional unit adjacent to $R^2$ may be a constitutional unit represented by the following formula:

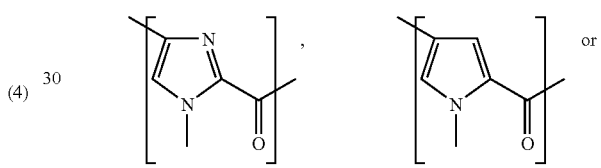

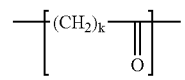

(wherein k is an integer of 0 to 10).

2. The indole derivative according to claim 1, wherein $R^2$ represents an acetyl group.

3. The indole derivative according to claim 2, wherein the indole derivative is represented by formula (3-1):

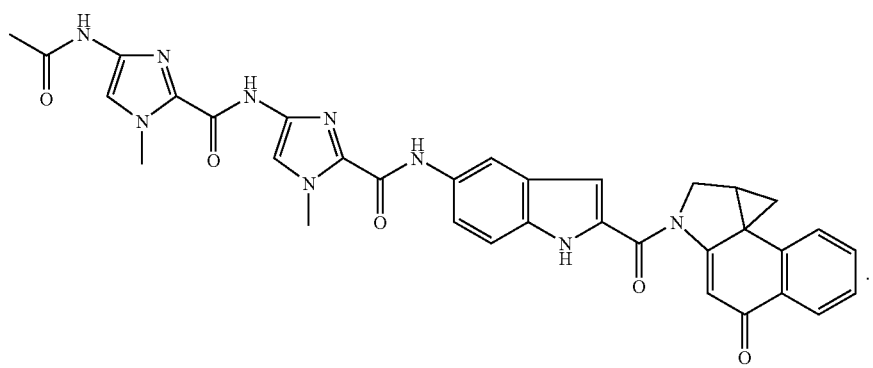
(3-1)

4. The indole derivative according to claim 2, wherein the indole derivative is represented by formula (3-2):
(3-2)
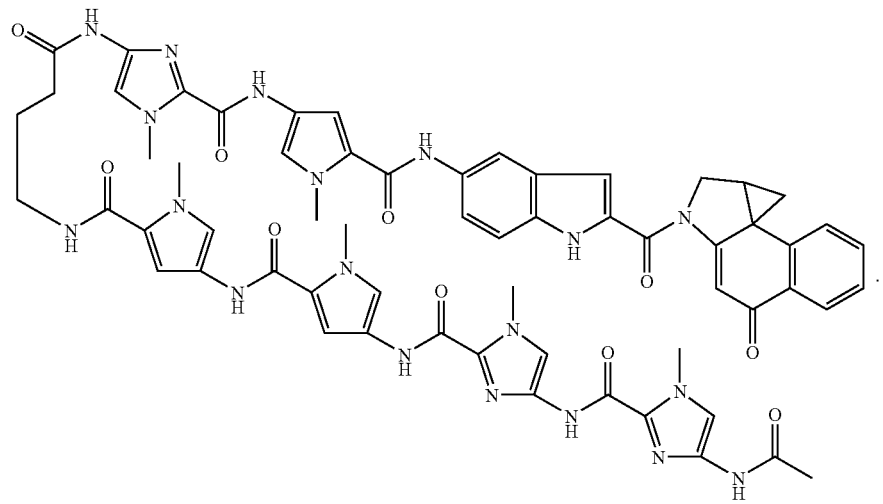
5. The indole derivative according to claim 2, wherein the indole derivative is represented by formula (3-3):
(3-3)
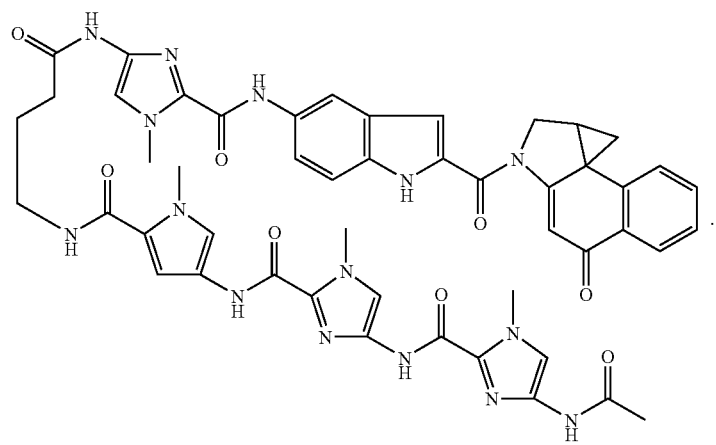
6. The indole derivative according to claim 2, wherein the indole derivative is represented by formula (3-4):
(3-4)
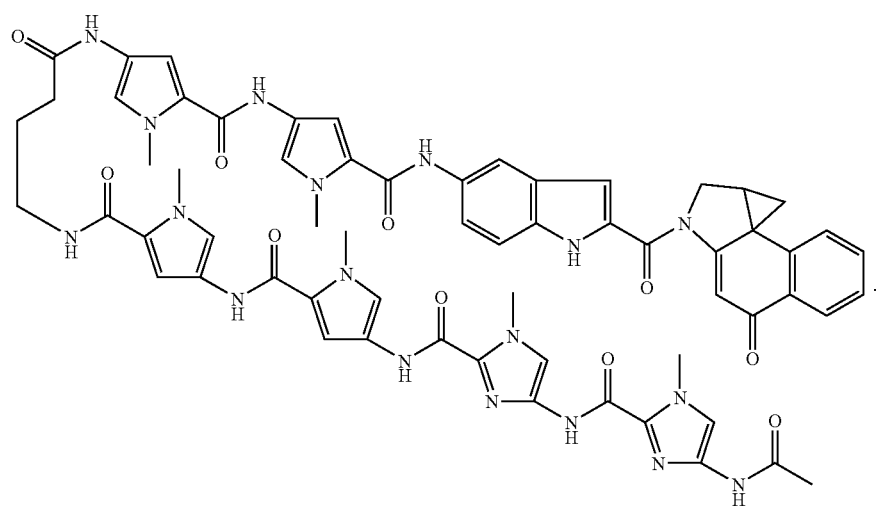

7. The indole derivative according to claim 2, wherein the indole derivative is represented by formula (3-5):
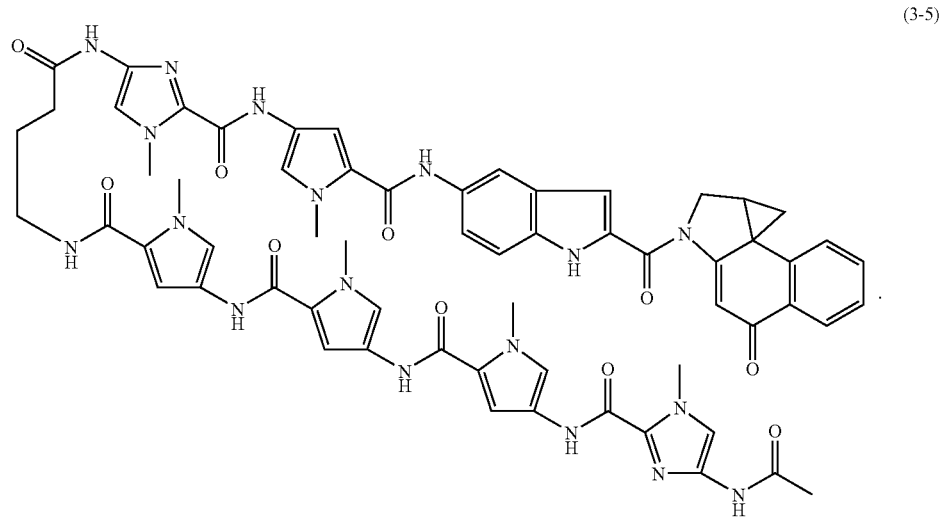
(3-5)
8. The indole derivative according to claim 2, wherein the indole derivative is represented by formula (3-6):
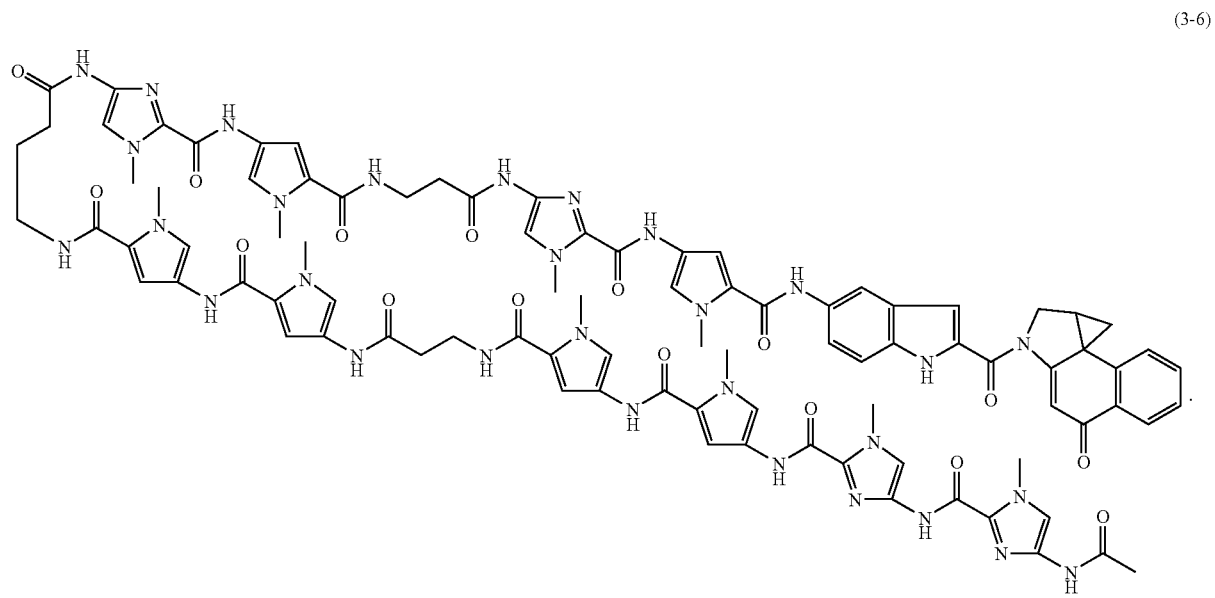
(3-6)

9. The indole derivative according to claim 2, wherein the indole derivative is represented by formula (3-7):
(3-7)
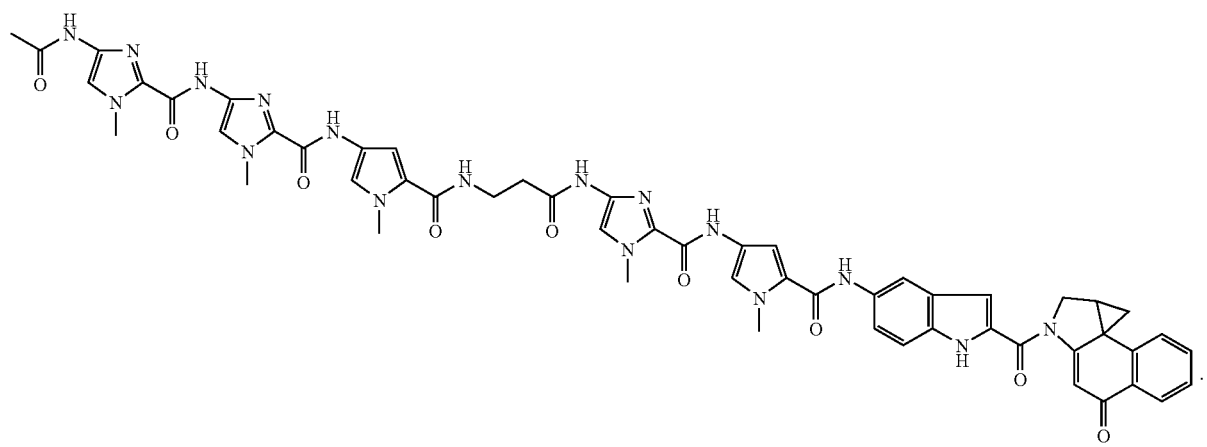
10. The indole derivative according to claim 3, wherein the indole derivative is represented by formula (4-1):
(4-1)
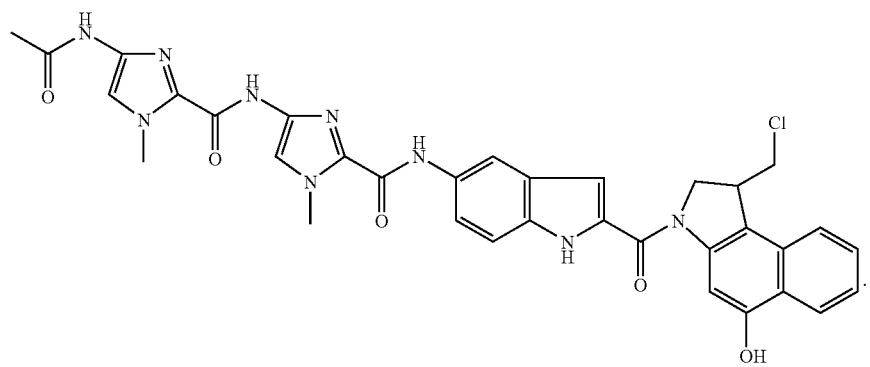
11. The indole derivative according to claim 2, wherein the indole derivative is represented by formula (4-2):
(4-2)
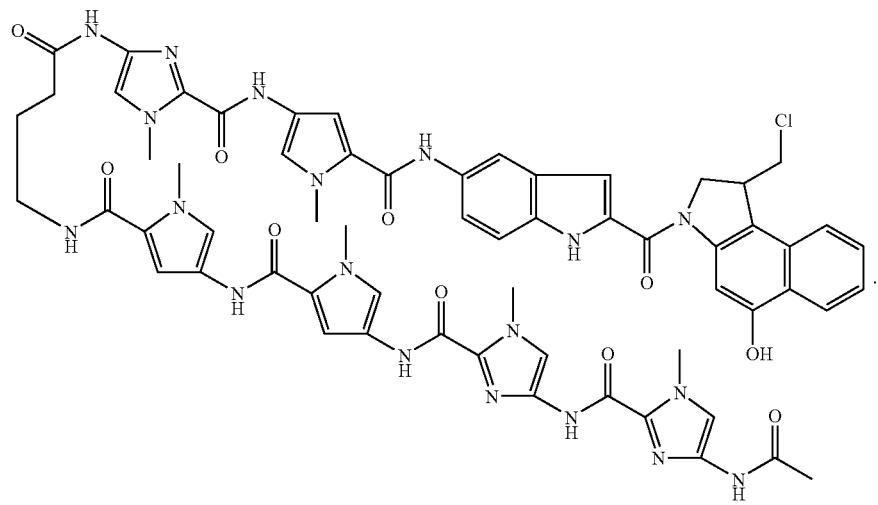

12. The indole derivative according to claim 2, wherein the indole derivative is represented by formula (4-3):

(4-3)

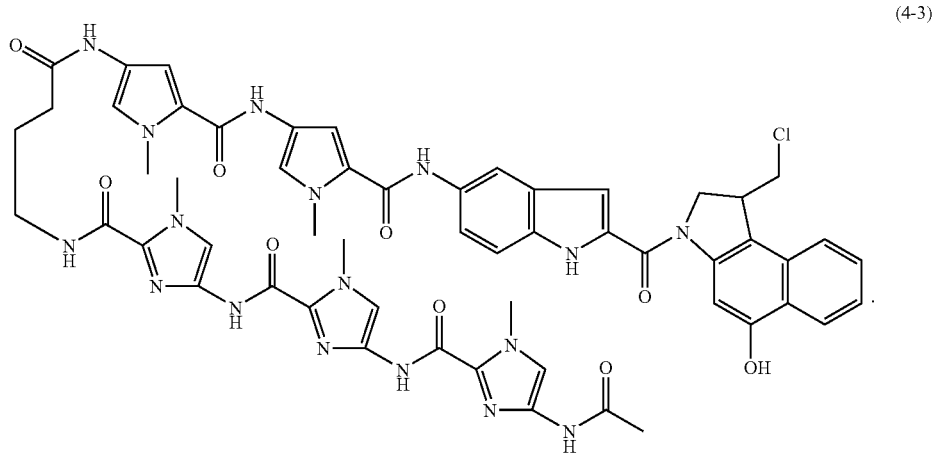

13. An alkylating agent for alkylating DNA, wherein the alkylating agent is composed of the indole derivative according to claim 1.

14. The alkylating agent for alkylating DNA according to claim 13, wherein the indole derivative has a hairpin structure and thus recognizes DNA.

15. The alkylating agent for alkylating DNA according to claim 13, wherein the indole derivative dimerizes to recognize DNA.

16. The alkylating agent for alkylating DNA according to claim 13, wherein the alkylating agent further contains a compound having two or more constitutional units which may be the same or different, the constitutional unit being represented by the following formula:

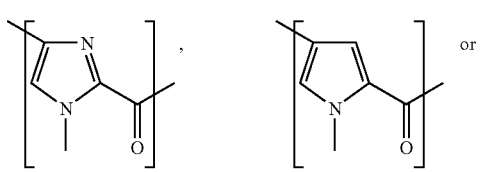

(wherein n is an integer of 0 to 10), wherein among the constitutional units, a terminal constitutional unit adjacent to an N-terminus may be a constitutional unit represented by the following formula:

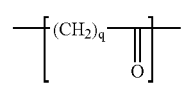

-continued

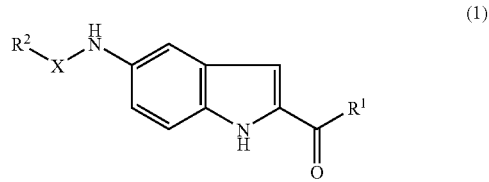

(wherein q is an integer of 0 to 10).

17. An alkylating agent for alkylating DNA, wherein the alkylating agent is composed of the indole derivative according to claim 1.

18. An indole derivative represented by general formula (1):

(1)

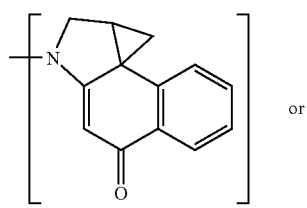

wherein $R^1$ represents by the following formula:

(3)

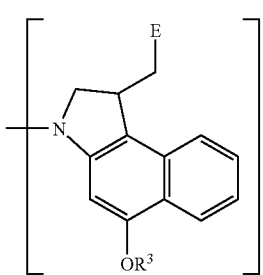

(4)

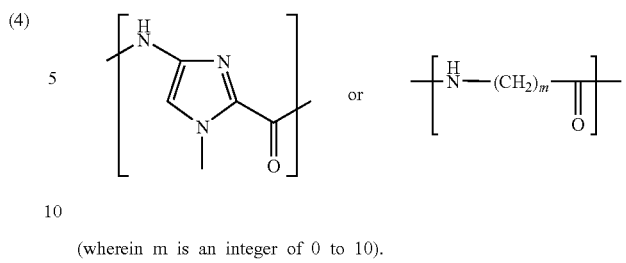

(wherein m is an integer of 0 to 10).

(wherein in formula (4), $R^3$ represents a hydrogen atom, a peptide chain, a carbohydrate chain, or a polyethylene glycol group; and E represents an elimination group selected from the group consisting of a halogen atom, a mesyl group, and a tosyl group); $R^2$ represents a hydrogen atom, an alkyl group, or an acyl group; and X represents a divalent group having one constitutional unit, the constitutional unit being represented by the following formula:

19. The indole derivative according to claim 1, wherein $R^2$ represents an acetyl group.

20. An alkylating agent for alkylating DNA, wherein the alkylating agent is composed of the indole derivative according to claim 18.

* * * * *